US011488713B2

(12) United States Patent
Velez et al.

(10) Patent No.: US 11,488,713 B2
(45) Date of Patent: Nov. 1, 2022

(54) DISEASE SPECIFIC ONTOLOGY-GUIDED RULE ENGINE AND MACHINE LEARNING FOR ENHANCED CRITICAL CARE DECISION SUPPORT

(71) Applicant: Computer Technology Associates, Inc., Cardiff, CA (US)

(72) Inventors: Carmelo Velez, Encinitas, CA (US); Timothy Tschampel, Ashburn, VA (US); Emilia Apostolova, Chicago, IL (US); Adam Boris, Cardiff, CA (US)

(73) Assignee: Computer Technology Associates, Inc., Cardiff, CA (US)

( * ) Notice: Subject to any disclaimer, the term of this patent is extended or adjusted under 35 U.S.C. 154(b) by 1114 days.

(21) Appl. No.: 15/998,436

(22) Filed: Aug. 15, 2018

(65) Prior Publication Data

US 2019/0057774 A1 Feb. 21, 2019

Related U.S. Application Data

(60) Provisional application No. 62/545,908, filed on Aug. 15, 2017.

(51) Int. Cl.
*G16H 50/20* (2018.01)
*G16H 70/60* (2018.01)
(Continued)

(52) U.S. Cl.
CPC ............ *G16H 50/20* (2018.01); *G06N 20/00* (2019.01); *G16H 10/40* (2018.01); *G16H 10/60* (2018.01);
(Continued)

(58) Field of Classification Search
CPC ........ G16H 50/20; G16H 10/40; G16H 10/60; G16H 20/00; G16H 50/50; G16H 70/60; G06N 20/00; G06N 7/005; G06N 5/022
See application file for complete search history.

(56) References Cited

U.S. PATENT DOCUMENTS

| 7,805,385 B2 * | 9/2010 | Steck ..................... G16H 50/20 |
| | | 706/10 |
| 2007/0255666 A1 * | 11/2007 | Sanfilippo .............. G06N 7/005 |
| | | 706/12 |

(Continued)

FOREIGN PATENT DOCUMENTS

| EP | 3255573 A1 * 12/2017 ............. G06F 19/00 |
| WO | WO-2016065293 A1 * 4/2016 ....... G06F 17/30864 |

*Primary Examiner* — Ryan W Sherwin
(74) *Attorney, Agent, or Firm* — Select Patents; Ashkon Cyrus

(57) ABSTRACT

A disease-specific ontology crafted by a consensus of expert clinicians may be used to semantically characterize/provide semantic meaning to dynamically changing patient electronic medical record (EMR) data in critical care settings. Hierarchical, directed node-edge-node graphs (concept maps or Vmaps) developed with an end-user friendly graphical user interface and ontology editor, can be used to represent structured clinical reasoning and serve as the first step in disease-specific ontology building. Disease domain Vmaps reflecting expert clinical reasoning associated with management of acute illnesses encountered in critical care settings (e.g. ICUs) that extend core clinical ontologies, developed and reviewed by experts, are in turn extended with existing medical ontologies and automatically translated to a domain ontology processing engine. Semantically-enhanced EMR data derived from the ontology processing engine is incorporated into both real-time 'track and trigger" rule engines and machine learning training algorithms using aggregated data. The resulting rule engines and machine-learnt models provide enhanced diagnostic and prognostic information respectively, to assist in clinical dual modes of reasoning (analytical rules and models based on experiential data) to assist in decisions associated with the specific disease in acute critical care settings.

14 Claims, 18 Drawing Sheets

(51) Int. Cl.
*G16H 50/50* (2018.01)
*G06N 20/00* (2019.01)
*G16H 20/00* (2018.01)
*G16H 10/40* (2018.01)
*G16H 10/60* (2018.01)

(52) U.S. Cl.
CPC ............ G16H 20/00 (2018.01); G16H 50/50 (2018.01); G16H 70/60 (2018.01)

(56) References Cited

U.S. PATENT DOCUMENTS

| | | | |
|---|---|---|---|
| 2010/0094874 A1* | 4/2010 | Huber | G16H 50/20 707/E17.014 |
| 2015/0046388 A1* | 2/2015 | Sheth | G06N 5/022 706/55 |
| 2015/0261925 A1* | 9/2015 | Wang | G16H 15/00 705/2 |
| 2018/0068083 A1* | 3/2018 | Cohen | G16B 40/20 |
| 2018/0075194 A1* | 3/2018 | Allen | G16H 70/20 |
| 2018/0349555 A1* | 12/2018 | Devarakonda | G16H 50/20 |

* cited by examiner

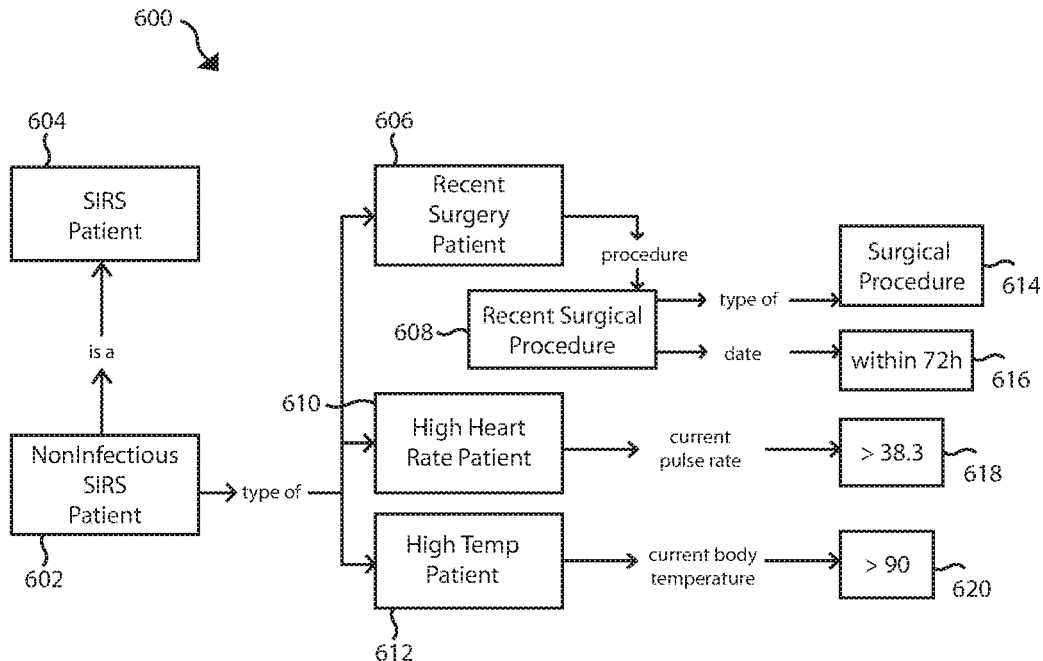

Automatically Generated First Order Logic Rules Snippets

```
rule "High Temp Patient"
no-loop
when
    IDA ($a:i)
    OPAA(s--$a, pid=="core:state", $state:o)
    DPAA("s--$state, pid=="core:currentBodyTemperature", Float parseFloat(o.getValue())>38.3
then
    CAA caa = new CAA("example::High_Temp_Patient", $a);
    insertLogical(caa)
    inferrer.inferLogical(caa);
end
```

```
rule
"SIRS NonInfection Patient"
no-loop
when
    IDA($a:1)
    CAA(cid=="core:Patient", i==$a)
    not(
        CAA(cid=="example::RecentSurgeryPatient", i==$a)
    )
    CAA(cid=="example::HighTempPatient", i==$a)
    CAA(cid=="example::HighHeartRatePatient", i==$a)
then
    CAA caa = new CAA("example:NonInfectionSIRSPatient",
    $a); insertLogical(caa);
        inferrer inferLogical(caa);
end
```

| Model | Composite Risk/Outcome | Dataset Labels | Algorithm | AUC (95% CI) |
|---|---|---|---|---|
| PCM1a | (none or SIRS) -> Sepsis | ICD-9 | Lasso | .87 (.79, .92) |
| PCM1a | (none or SIRS) -> Sepsis | SCT | Lasso | .97 (.91, .99) |
| PCM1b | (infection) -> Sepsis | SCT | DBN | .96 (.95, .96) |
| PCM2 | (non or SIRS or Sepsis) -> any severe Sepsis | ICD-9 | Lasso | .91 (.83, .96) |
| PCM2 | (non or SIRS or Sepsis) -> any severe Sepsis | SCT | Lasso | .98 (.93, .99) |
| PCM3 | (any severe Sepsis) -> Mortality | SCT | Cox | .95 (.93, .97) |

Abbreviations:

PCM = predictive clinical model (e.g. PCM1b predicts sepsis in infected ICU patients);

SCT = septic screening tool

ICD-9 = patient discharge codes as recorded in EMR;

Lasso = Least absolute shrinkage and selection operator logistic regression with forward and backward stepwise selection;

Cox = Survival analysis with Time Dependent Covariates and Censoring;

DBN = Dynamic Bayesian Network, 5-time slices;

AUC = area under ROC curve (C-statistic);

CI = confidence interval;

FIG.7

DISEASE SPECIFIC ONTOLOGY-GUIDED RULE ENGINE AND MACHINE LEARNING FOR ENHANCED CRITICAL CARE DECISION SUPPORT

This application claims priority to provisional application 62/545,908, filed 2017 Aug. 15.

FIELD OF THE INVENTION

One or more embodiments relate to systems and methods for providing disease specific ontology-guided rule engines and machine learning techniques for enhanced critical care decision support.

BACKGROUND OF THE INVENTION

Automated, rule-based clinical decision support ("CDS") technology used with electronic medical record ("EMR") data has been shown to provide promising benefits in improving clinician situational awareness in critical care settings. However, in general CDS tools available today used to monitor changes in bedside physiological data are designed to "cast a wide net", generating alerts that generally "insufficiently specific." Therefore, alerts from such tools are commonly ignored. While some rule-based tools improve rule-based CDS specificity performance by increasing clinical criteria risk thresholds to detect only the most seriously ill, when used in actual clinical practice, such augmented rule-based tools can be "insufficiently sensitive", and miss identifying important, less obvious cases that remain unrecognized in early stages of clinic deterioration that could benefit from early interventions.

Current CDS tools are limited to relatively rudimentary rule logic over observed data (e.g. when vital signs or lab results exceed pre-specified thresholds). By failing to reflect the complex clinical reasoning used by expert clinicians to make patient-specific decisions based on combining observed signatures in potentially numerous observed data elements and associated trends with the specific patient context, with recent evidence/guidelines, and, most importantly, with expert clinician experience based on years of practice, these rule-based CDS tools generate alerts that are ignored and result in what is commonly called "alert fatigue". Alert fatigue (high rates of alert overrides) is now a pressing and prevalent problem in medicine. Physicians and other providers appear to override computerized alerts stemming from current EMR systems between 49% up to 96% of the time, even clinically important alerts. Without effective CDS tools, medical errors in critical care are common and cause morbidity and mortality in critically ill patients. Recently, calls to improve CDS for diagnostic reasoning have gained increased support. In summary, the use of current CDS tools based on rudimentary logic, usually found as embedded logic in commercially available EMR systems, have not, in general, served to improve patient outcomes such as reduced mortality of critically ill patients under care in hospitals.

Studies show that there are two models of clinical reasoning used by clinicians to make decisions: 1) experiential, described as heuristic, tacit, quick, intuitive, recognition primed, implicit, acquired by exposure; 2) rule-based, described as rational, conscious, deliberate, slow, analytic, and explicit. CDS tools may support these dual modes of reasoning with evidence-based rule engines trained by experts and supervised machine learning techniques that can be similarly "trained" to recognize clinical experiential patterns in Electronic Medical Record ("EMR") real-time data streams using historical clinical data repositories.

Using abstracted cohort EMR training data, ML techniques can be used to derive predictive models that identify patterns in non-specific clinical data (e.g. physiological time series) associated with an outcome (e.g. mortality, life threatening illness, extended length of stay ("LOS"), readmission), potentially identifying patients who could benefit from preventive treatment. The ability for ML techniques to detect/recognize subtle signatures of incipient illness probabilistically associated with diverse physiological data hours prior to detectability by clinical staff is an important, promising advantage of ML-based CDS over rule-based CDS.

Disadvantages of current ML-based CDS techniques include noisy patient EMR training data skewing the predictive performance of such techniques, and leading to degraded ML performance and unintended consequences. For example, for acute syndromic diseases like sepsis or acute respiratory distress syndrome ("ARDS") that frequently accompany comorbid conditions, "gold standard" outcome classification codes (e.g. ICD-9/10) are frequently in error or missing in critical care EMR records. Traditional machine learning over EMR data may rely on the presence of accurate diagnostic coding "case labels" for supervised training. ML models derived using high levels of training data "label noise" (e.g. more than one-half of patients with severe sepsis are not documented to have this diagnosis by their physicians) may significantly degrade ML predictive performance associated with such diseases and result in unintended consequences. Similarly, physiological data can be missing or contextually mischaracterized or lacking context, thus resulting in "feature noise" (e.g. training data that fails to discriminate observed abnormal physiological EMR training data features as "acute" responses to new insults as opposed to chronic conditions or "normal responses" to treatments). Moreover, EMR data is challenging to represent and model for machine learning due to its high dimensionality, temporally dynamic, noise, heterogeneity, sparseness, incompleteness, random errors, systematic biases and lack of semantic harmony. For example, the same clinical phenotype can be expressed using different codes and terminologies: a patient diagnosed with "type 2 diabetes mellitus" can be identified by laboratory values of hemoglobin A1C greater than 7.0, presence of 250.00 ICD-9 code, "type 2 diabetes mellitus" mentioned in the free-text clinical notes, and so on. These challenges make it difficult for machine learning methods to identify patterns that produce sufficiently precise predictive clinical models for real-world applications. Recent studies show that in cases of missing context, poor concept harmonization or feature/label noise, models trained without raw data enhancements that address these issues can result in technically valid but dangerously misleading machine learning prognostic models.

Additionally, many popular ML tools such as neural networks with "hidden layers" operate as "black boxes" over EMR data, where the rationale for the outputs is unavailable. Unlike rule-based systems where the logic that triggers a rule can be easily understood, with tools such as neural networks, there is no logical flow that a human can understand. Without causal clarity, predictions from such tools may not be useful in life-threatening critical care scenarios. Moreover, predictive ML models derived from EMR training data need to be updated periodically to reflect contemporary practice/protocols and institution-specific patient demographics. Current retraining/recalibration of predictive models based on changing practice/protocols or institution-specific patient populations is generally labor intensive.

Consequently, ML based CDS tools are not yet widely used in bedside workflows.

SUMMARY OF THE INVENTION

One or more embodiments described herein provide benefits and/or solve one or more of the foregoing or other problems in the art with automated clinical decision support tools based on rule engines and ML-based predictive models used in critical care. Embodiments of the invention disclose problem-specific contextually-rich ontological models that model the clinical reasoning of critical care expert clinicians to significantly improve actionable performance of automated CDS in the analysis of EMR physiological and patient narrative data towards enhanced early recognition and treatment of at risk patients. These ontological models support the exposure of the semantic characterizations and expert interpretations of features that are then used as training data to properly train ML algorithms that can help bedside clinicians accurately recognize and explore, as experts, the implications of observed physiological time series and recorded structured and free text EMR feature data. Additionally, by automation of the "pipeline" between the disease-specific ontology and EMR data reuse, frequent highly automated "big data" updates to predictive models is enabled.

The preferred embodiment of this disclosure utilizes highly intuitive graphical VFusion concept maps (hereby referred to as "Vmaps") developed using an ontology editor and user interface that capture the detailed structured reasoning of collaborating multidisciplinary expert clinicians used to interpret patient physiological data, typically extending evidence-based guidelines, reflecting deep expertise derived from years of experience in the management of critical diseases. The present disclosure provides a Vmap editor that can be used to graphically view and describe editorial changes to an existing ontology (e.g. edit ontological class structures, properties/relationships or rules) and/or create a new ontology These intuitive graphical expressions form the foundations of a comprehensive customized ontology that can be used by semantic reasoners, rule engines and machine learning for disease-specific CDS applications. Specifically, Vmaps graphically describe clinical reasoning that is used to derive a comprehensive disease specific computable ontology that can subsequently be used with raw EMR data to semantically identify cohorts and characterize/interpret clinical features that support the dual rule-based/experiential reasoning processes of physicians, influencing production rules, natural language processing (NLP), and the machine learning discovery process with the deep expertise, heuristics, and knowledge of subject matter experts.

DESCRIPTION OF FIGURES

To describe the way the above recited and other advantages and features of one or more embodiments can be obtained, a more particular description will be rendered by reference to specific embodiments thereof that are illustrated in the accompanying drawings. These drawings depict only typical embodiments and are not therefore considered to be limiting of its scope. Accordingly, various embodiments will be described and explained with additional specificity and detail using the accompanying drawings.

FIG. 6 illustrates a small snippet of ontological logic according to an embodiment of the present disclosure.

FIG. 7 shows some sample C-statistic results comparing the use of semantic characterizations (SCT) for training ML algorithms (e.g. training Lasso logistic regression using semantically enriched features and labels) against training Lasso using traditional EMR raw features and coded outcomes data (ICD-9) according to an embodiment of the present disclosure.

FIG. 8a) is used to derive a machine learning based NLP algorithm to detect a target feature (e.g. infection) from free text notes.

DETAILED DESCRIPTION

Figure 1A:
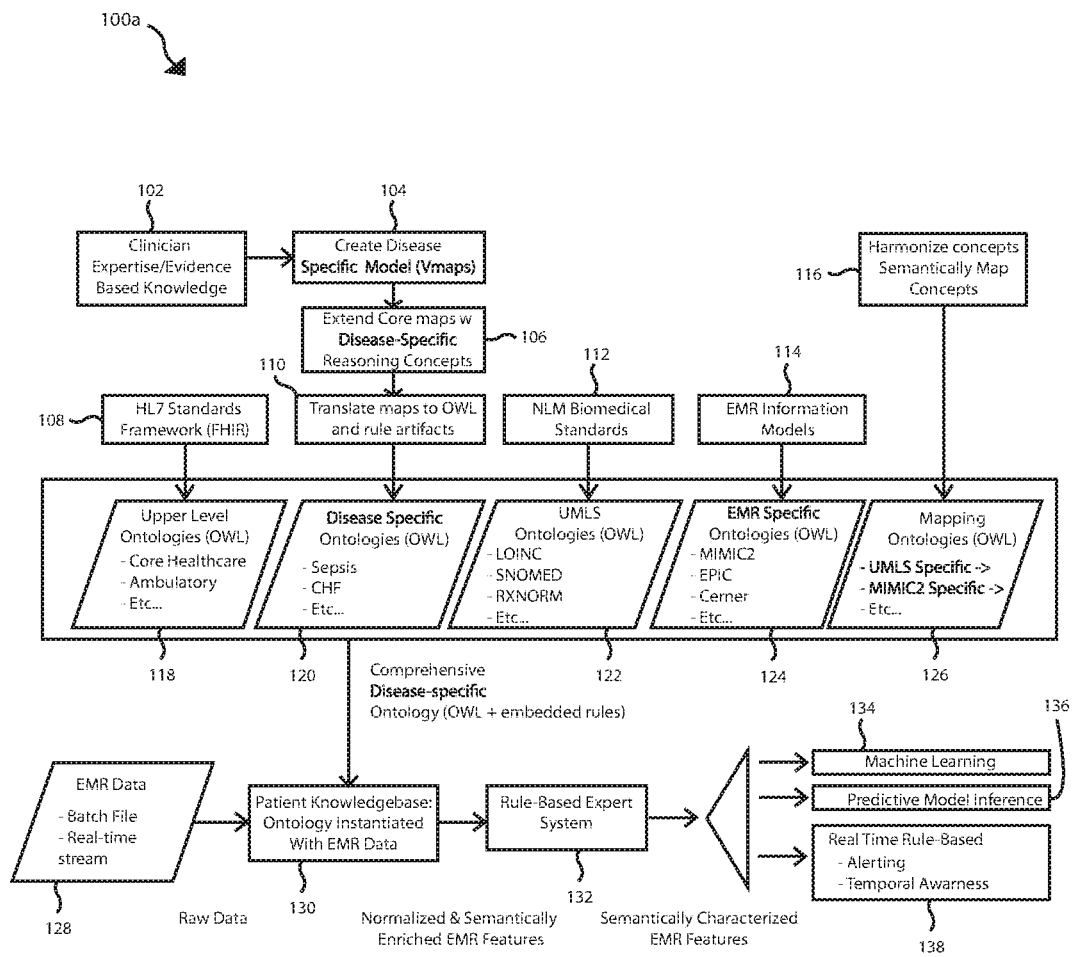
FIG. 1a is a functional processing flow of a combined rule engine and machine learning CDS according to an embodiment of the present disclosure.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

The preferred embodiment of the present disclosure includes functional processes and systems for creation and use of customized disease specific ontologies in clinical decision support. In the domain of healthcare and biomedical informatics, several different general purpose ontological repositories have been developed including the Unified Medical Language System (UMLS), a set of files and software that brings together many health and biomedical vocabularies and standards to enable interoperability between computer systems at the "raw data" level. The key UMLS knowledgebase used is the Metathesaurus (including concepts from many vocabularies including ICD, SNOMED, LOINC, RXNORM, and CPT), and the Semantic Network consisting of (1) a set of broad subject categories, or semantic types, that provide a consistent categorization of all concepts represented in the UMLS Metathesaurus, and (2) a set of useful and important relationships, or semantic relations, that exist between semantic types.

Customized medical ontologies extend these general purpose ontologies to provide expert information associated with one or more specific diseases and numerous medically relevant concepts associated with clinical information typically captured in EMRs in both structured and free text forms used in the management of the specific disease (e.g., disease-relevant physiological findings, laboratory findings, diagnostic procedures; medications, therapeutic procedures, clinical history, symptoms, radiological assessments; clinical impressions, and others). Different relationships, known by experts based on medical evidence or practice experience, between concepts are reflected by the disease-specific domain ontology. For example, different names for a same concept or class-subclass relationships can be expressed using an "IS A" or "TYPE OF" type relationship. Expressions of one or more patient state observations (e.g. "high temperature patient", "tachycardia patient", "recent surgery patient") relating a patient with an abnormal finding or high risk class relevant to the disease specific domain (e.g. sepsis), and related contextual features such as date/time stamps of findings or procedures, trends, providers/locations associated with such events, inferences such as "MAY INDICATE" potentially associating a constellation of findings (e.g. demographics, signs, symptoms, trends, medical history, genetic data, and others) with a disease state based on expert knowledge and experience are other examples of types of relationships in the ontology. Ontological classes can also be combined with first order logic rule structures and/or "ontology reasoners" to support complex inferencing/reasoning patterns such as temporal event reasoning, truth maintenance, incremental reasoning, as well as supporting assertion explanations.

The present disclosure further provides for establishing an explicit formal specification of the concepts in a particular disease specific domain and relations among them reflective of both the evidence base and expert knowledge/experience of multidisciplinary practicing clinicians, the customized ontologies of the preferred embodiment of the present disclosure, combined with UMLS, can provide the basis for reusing and integrating valuable, highly competent evidence- and experienced-based domain knowledge and clinical reasoning within decision support applications using routinely captured patient EMR data.

Clinical applications must often deal with large volumes of complex information originating from different sources, with different structures, and with different semantics. Clinical information in diverse EMRs is often structured to produce a vast number of diverse standards and conceptual vocabularies that make reuse in medical analytics difficult. Beyond diverse syntax used to express clinical concepts, the semantic "meaning" of any specific item of information may be contextually dependent (e.g. high fever may be "normal" in a new postsurgical patient and "abnormal" in an immunocompromised patient). It can be appreciated that UMLS and the custom mapping and reasoning ontologies herein described in the present disclosure may be used to semantically integrate and semantically enhance these information resources.

Turning now to the drawings, FIG. 1a is a functional processing flow of a combined rule engine and machine learning CDS according to an embodiment of the present disclosure. FIG. 1a discloses a high-level block diagram of a functional processing flow of the combined rule engine and machine learning CDS that includes a disease-specific ontology and associated rules subsystem for enhanced CDS performance in critical care settings.

The upper components of FIG. 1a describe the basic elements of the derivation of a disease-specific comprehensive ontology (120), such as a disease-specific upper level ontology extended with granular clinical classes and relationships in a specific domain such as diagnoses (ICD), laboratory tests (LOINC), and medications (RXNORM). At steps 102 and 104, high level graphical representations (Vmaps) of conceptual clinician expertise and evidence-based knowledge of the specific disease specific domain are authored by collaborating multidisciplinary clinicians via the VFusion Vmap editing interface (or an equivalent). At step 106, the core maps created are extended with disease-specific reasoning concepts representing heuristics used by experts to interpret confounding/complex EMR data streams (e.g. common sources of cognitive medical errors). These extended maps representing the combination of evidence- and practice-based knowledge (e.g. heuristics) are then translated into web ontology language (OWL) ontologies and rule artifacts (step 110) to form the Disease Specific Ontologies and associated embedded rules in step 120. OWL is a computational logic-based language used by the bioinformatics community such that diverse knowledge expressed in OWL can be integrated and exploited by diverse "reasoner" and "rule engine" applications and can be published in the World Wide Web and may refer to or be referred from other OWL ontologies. The system also provides for integration with "upper level" ontological healthcare domain modules 118 and UMLS Ontologies 122, EMR Specific Ontologies 124, and Mapping Ontologies 126.

Disease specific ontologies 120 for diseases such as sepsis may have classes such as "patient" and "antibiotic", "immune system compromising chronic conditions" (e.g. cancer, HIV, transplants, etc.) with patient subclasses "infected patient" defined by the property "using non-prophylactic antibiotic" and "high sepsis risk" defined by the property "has immune system compromising chronic condition". The extensive RXNORM antibiotics class ontology structure could be associated with the "antibiotic" class in the disease specific ontology thereby extending the class structure and rules and enable automated harmonization of infected patients with EMR data that may reflect use of numerous differing types of antibiotic medications.

Disease specific ontologies 120 may also express first order logic rules that reflect complex clinical reasoning over EMR data classes (e.g. in the sepsis domain, "a patient is in the class 'infected patient' if the patient is 'using antibiotic' and 'antibiotic NOT prophylactic antibiotic', a patient with high fever immediately following cardiac bypass surgery is NOT sufficient evidence of infection risk, or a cancer patient with moderate fever is in the class "high sepsis risk"). It can be appreciated that these first order logic rules allow for targeted disease-specific queries.

Medical ontologies contain groupings that are common across multiple healthcare domains (e.g. care settings such as Ambulatory, Emergency Rooms (ERs), Intensive Care Units (ICUs), general wards, nursing homes) as well as disease domains (e.g. sepsis, ARDS, acute kidney disease, hemorrhage). This serves to enable interoperability across care setting and disease states. For example, the CDS tracking of patients using combinations of ambulatory, ER, ICU data, and/or the simultaneous tracking of multiple critical care diseases using a common core ontology and a semantically interoperable set of disease-specific ontologies.

For example, patients with chronic congestive heart failure (CHF) can have signs/symptoms that mimic sepsis (e.g. shortness of breath). The contextual knowledge in combined CHF/Sepsis ontologies can be used to help clinicians distinguish a septic patient from those with a CHF exacerbation to help guide appropriate treatment. In general, when managing sepsis, differential diagnoses include consideration of cardiopulmonary disease (e.g. pneumonia from aspiration, heart failure, atrial fibrillation, pulmonary embolus, COPD), metabolic disorders (diabetes, adrenal insufficiency), gastrointestinal pathology (e.g. hemorrhage, gastroenteritis), hematologic disease (e.g. anemia, proliferative malignancies), and neurological disorders (e.g. traumatic bleeds, intoxication, dementia).

EMR specific and mapping ontologies 124 and 126 contain EMR information models and data normalization/harmonization mappings of various terms (e.g. proprietary codes) used to associate a medical feature representing the same (or similar) meaning for the concept found in diverse raw EMR data sources with a standard ontology (e.g. SNOMED, RXNORM, LOINC, ICD, etc.) and then use that standard ontology to semantically classify/enrich that raw EMR feature expression. For example, in a specific EMR, a medication may be identified by a proprietary code or name. EMR information data model 124 and mapping ontology 126 could be used to map the expression to the RXNORM ontology which would also provide the medication ingredients/classification, e.g. a broad-spectrum antibiotic.

Similarly, the disease specific ontology classes and rules can be used to semantically characterize features reflecting the knowledge/expertise of the practicing clinicians and evidence base. For example, an antibiotic might be characterized as a "prophylactic antibiotic" if supported by the ontological classification of the patient at risk of an infection based on ontological clinical reasoning over context data (e.g. antibiotic medication used peri-operatively, in a broad-spectrum category, prescribed for limited use, etc.). The ontology may also reflect reasoning underlying choice of the specific broad-spectrum antibiotic(s) in cases of physician suspicion of antimicrobial resistance in an elderly patient on long-term antibiotics.

In summary, the Comprehensive Disease-specific Ontology (OWL+embedded rules) of FIG. 1a illustrates that ontologies can be created and customized to express concepts, relationships and rules in a highly specific domain and be used in conjunction with generic UMLS medical ontologies 122 (such as SNOMED and others). In one embodiment, a plurality of ontologies may be used for the same disease and/or types of relationships. In the embodiments described herein, the disease specific and support ontologies described below reflect the combination of ontologies as necessary for EMR data normalization, harmonization, enrichment and semantic characterization of features for rule-based, NLP and machine learning-based disease specific decision support.

From a functional perspective, components 128, 130, 132, 134, 136 and 138 form a "pipeline" process performed by a processor and enabling the creation, enhancement and use of a disease-specific ontology for computer assisted clinical decision support in critical care settings. As indicated in FIG. 1a, the processor can ingest "native" EMR data 128 either as population level batch files or patient-specific real-time data streams from one or more EMRs. EMR specific ontologies, mapping ontologies and UMLS are used to semantically harmonize and "instantiate" ontology classes 130 associated with the disease specific ontologies. Disease specific ontology and rules are then used to semantically characterize and interpret ingested EMR data 132 used to derive expert system-based alerting 140 as well as serve as annotated training data for machine learning 134. Machine learning using annotated training is used to derive both NLP processing algorithms 136 as well as predictive models 138.

Figure 1B:
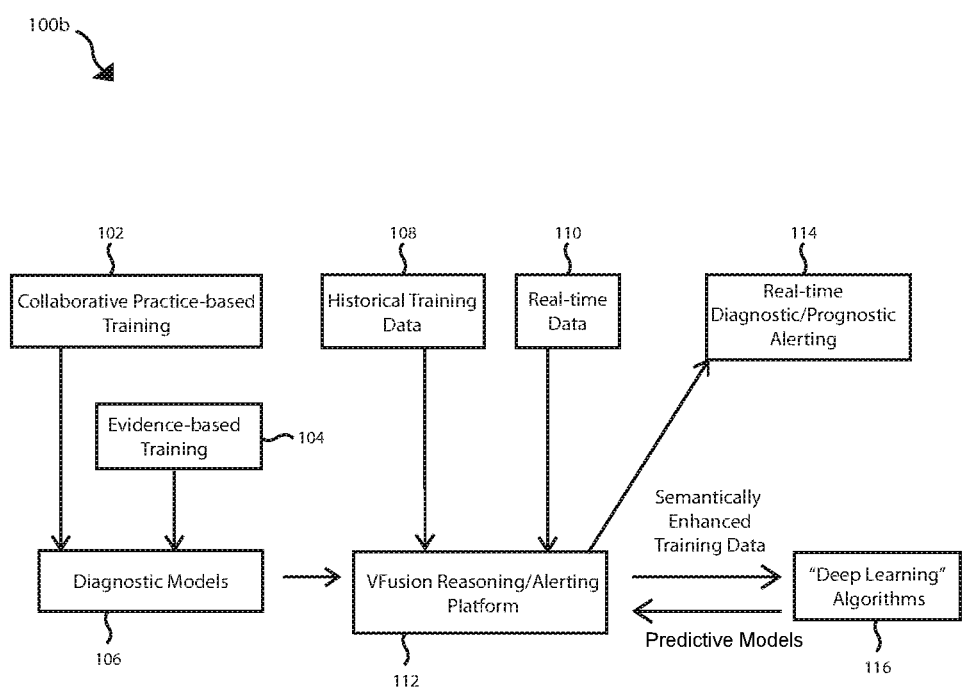
FIG. 1b is a physical processing flow of a combined rule engine and machine learning CDS according to an embodiment of the present disclosure.

FIG. 1b illustrates a VFusion physical processing flow which, in a specific embodiment, describes the sources of knowledge used to form the ontology, the flow of data from EMR for both machine learning and real time CDS assessments and how these tools generate alerts that are presented to bedside clinicians. Collaborative practice-based training data 142 and evidenced-based training data 144 are fed into rule-based diagnostic models 146, which are in turn used in the VFusion Reasoning/Alerting platform along with historical training data 148 and real time data 150. As an example of this, in the domain of sepsis there are 3 basic sources of knowledge used in VFusion for reasoning: 1) expert knowledge reflecting the evidence based training 144 typically documented in: a) guidelines (e.g. Surviving Sepsis Campaign (SSC) International Guidelines for Management of Sepsis and Septic Shock), b) consensus definitions in peer reviewed journals (e.g. The Third International Consensus Definitions for Sepsis and Septic Shock (Sepsis-3)), and c) many other related published sepsis management studies; 2) practice knowledge of collaborating clinicians to be used as practice-based training data 142 (e.g. for sepsis, how specialists in critical care, emergency medicine, infectious diseases, clinical pharmacy decide on initial/pre-culture empiric antibiotics) that deal with common confounders/complexities found in daily clinical practice; 3) historical records of patient data 148 retrospectively fed into the VFusion platform and then used by machine learning 156 to derive NLP and predictive algorithms which are fed back to the VFusion reasoning/alert platform. Real time data 150 is assessed using the combination 152 of the expert system reasoning derived from practice- and evidence-based knowledge and data driven NLP/predictive models derived from historical data to produce both real-time diagnostic (ontology/rule-based) as well as prognostic (prior experience-based predictive models) alerting 154.

Figure 1C:
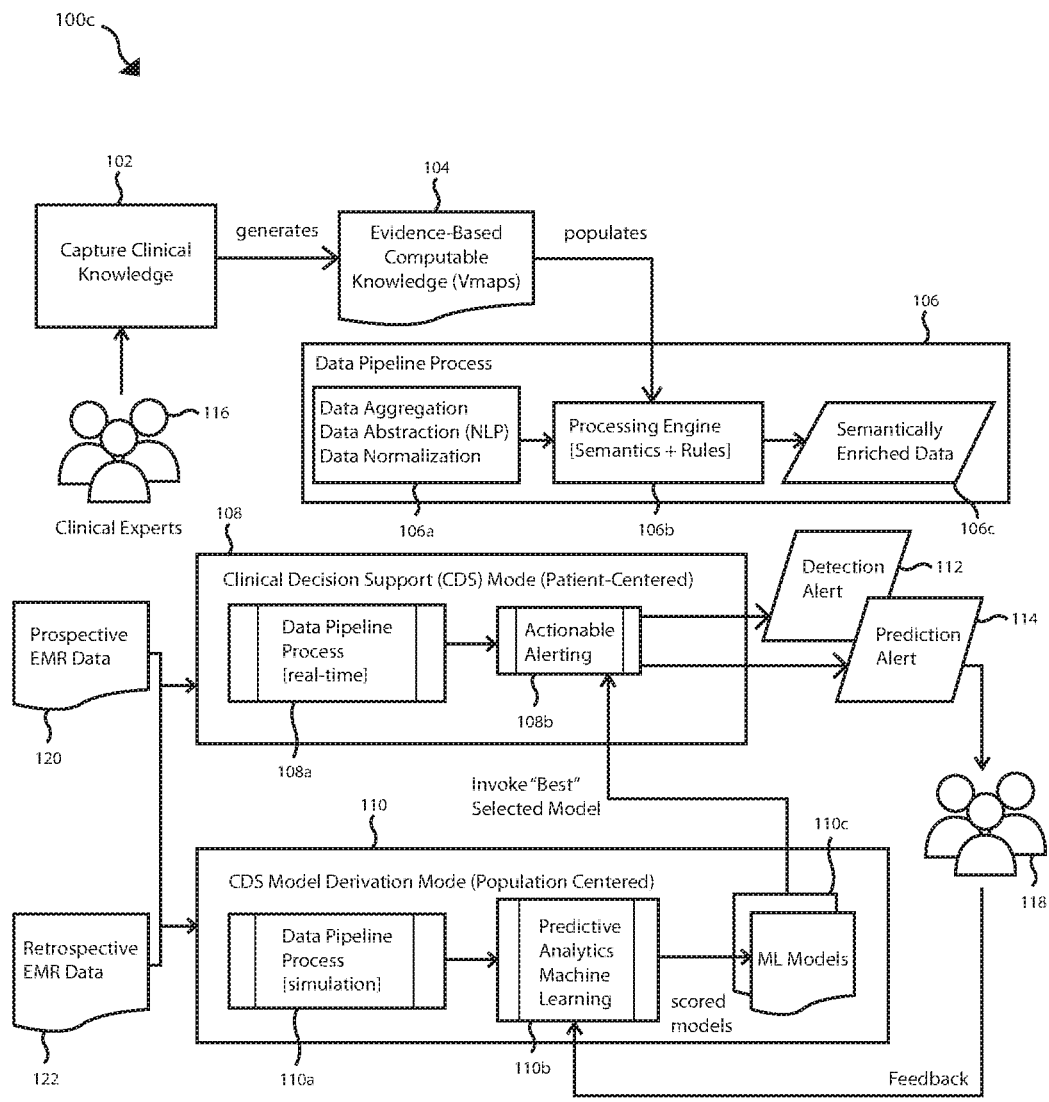
FIG. 1c is a functional architecture of a combined rule engine and machine learning CDS according to an embodiment of the present disclosure.

FIG. 1c illustrates a Vmap guided VFusion data pipeline process that is used both in retrospective CDS model derivation mode (machine learning) and prospective (real-time data assessments) CDS applied to new data for derivation of actionable alerting. VFusion Vmap editing and ontology services 162 are used by teams of clinical experts 160 to establish a practice- and evidence-based ontology which forms the basis of a semantics/rule-based processing engine 166b. The EMR information model and mapping components of the ontology and pretrained NLP algorithms are used to provide feature data aggregation, abstractions from free text, and data normalization services 166a. Aggregated, abstracted and normalized EMR features are then "processed" by the processing engine 166b using ontology to establish semantically enriched/classified disease-specific features 166c. Collectively, this data pipeline process 166 is used to process both real-time data streams 170 prospectively 168, 168a to generate rule-based detection (diagnostic) alerts 168b, 171 and semantically annotate large repositories of historical patient cohort data 172 for training machine algorithms using retrospective "batch" processing of data 174a. VFusion retrospective data processing can also support a "simulation" of real-time data streams for testing/pilot studies. Retrospective data processing mode uses semantically enriched feature training data 166c with a library of supervised and unsupervised machine learning algorithms 174*b* to derive ML trained models 174*c* that can then be used in prospective mode to evaluate new data and when appropriate, generate predictive (prognostic) alerts 168*b*, 173. Both rule-based diagnostic 171 and data-based prognostic 173 alerts can be presented to bedside clinicians 179 using diverse forms of alerting devices (e.g. mobile devices, EMR windows, etc.) Feedback from clinicians can be used to refine both sensitivity/specificity of the basis for rule-based diagnostic 164 and predictive analytics 174*b* prognostic alerting.

Figure 2:
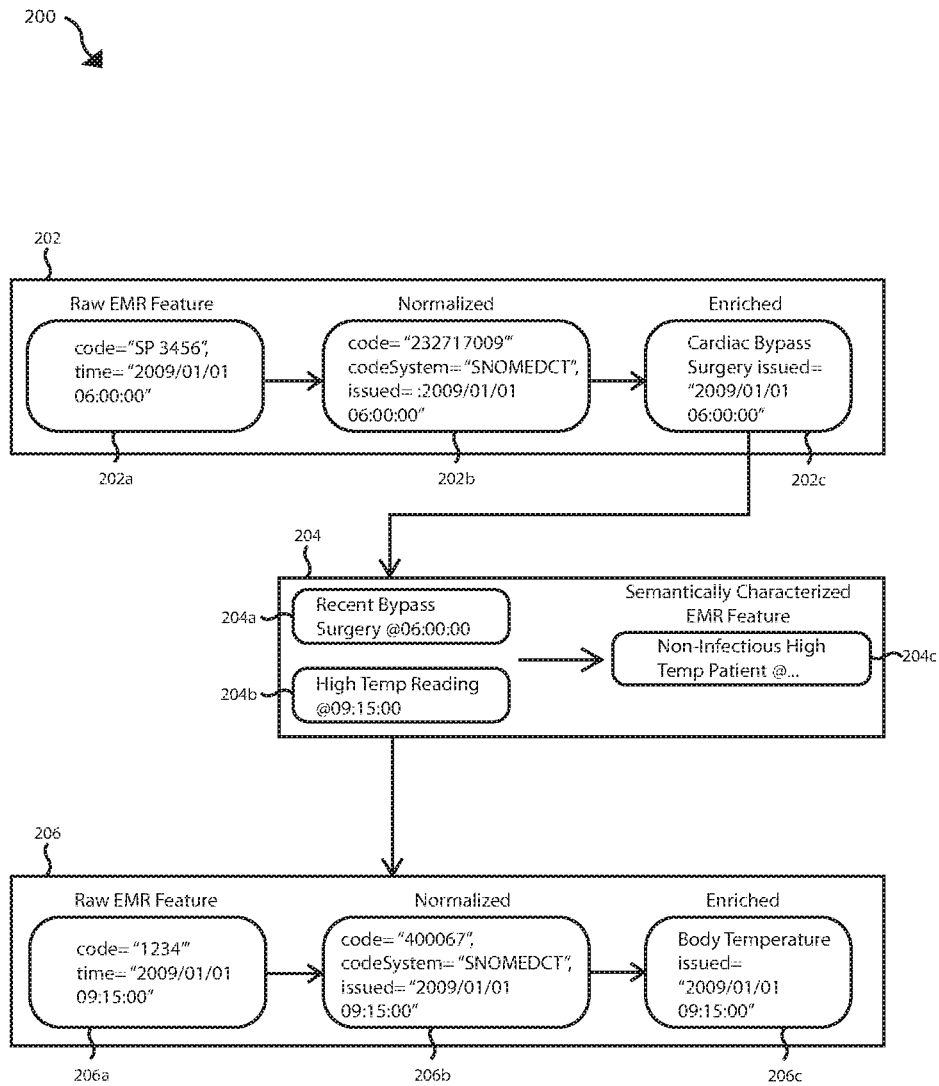
FIG. 2 is an example of normalization, enrichment and semantic characterization of data according to an embodiment of the present disclosure.

FIG. 2 illustrates examples of normalization, enrichment and semantic characterization of data. In the examples, EMR data recordings of vital sign observation such as body temperature at a given time 206 and recording a time-tagged surgical event 202 in the same patient record may be characterized by an EMR using EMR information model unique codes and value sets to represent these concepts. The disease-specific ontology that includes the EMR information model can be used to map the EMR unique codes to the semantically equivalent SNOMED code which in turn identifies the concepts in SNOMED as "Body Temperature" and "Cardiac Bypass Surgery" which, in turn, may be associated with concepts in the disease specific ontology. Assuming expert clinicians expressed reasoning that a cardiac bypass surgery can temporarily cause elevated body temperature within a 24 hour window, lacking other signs/symptoms of infection, a body temperature with an elevated value in a patient with recent surgery (as indicated by the proximity of relevant event times of the observation and surgery) may be semantically characterized for the designated period of 24 hours following surgery as "Non-Infectious High Temp Reading" 204 using the disease specific rules.

The processor can invoke one of many machine learning algorithms to create a predictive model using the semantically characterized training data. If more than one machine learning model is invoked, the system can either invoke the "best" performing model (e.g. performance on an independent test set as shown in FIG. 1*c*) or use ensemble methods that combine several machine learning techniques for enhanced predictive performance. The output of this ML process is a model that can be used as a CDS tool with new patient data to identify patients at risk of impending deterioration. The predictive performance of the learnt model is influenced by the semantic characterizations/interpretations of the training features guided by the disease-specific ontology. As new training data is aggregated, or as end user clinicians make changes to the disease-specific ontology, the pipeline process can be reused with either new data or ontology to improve predictive model performance.

Figure 3:
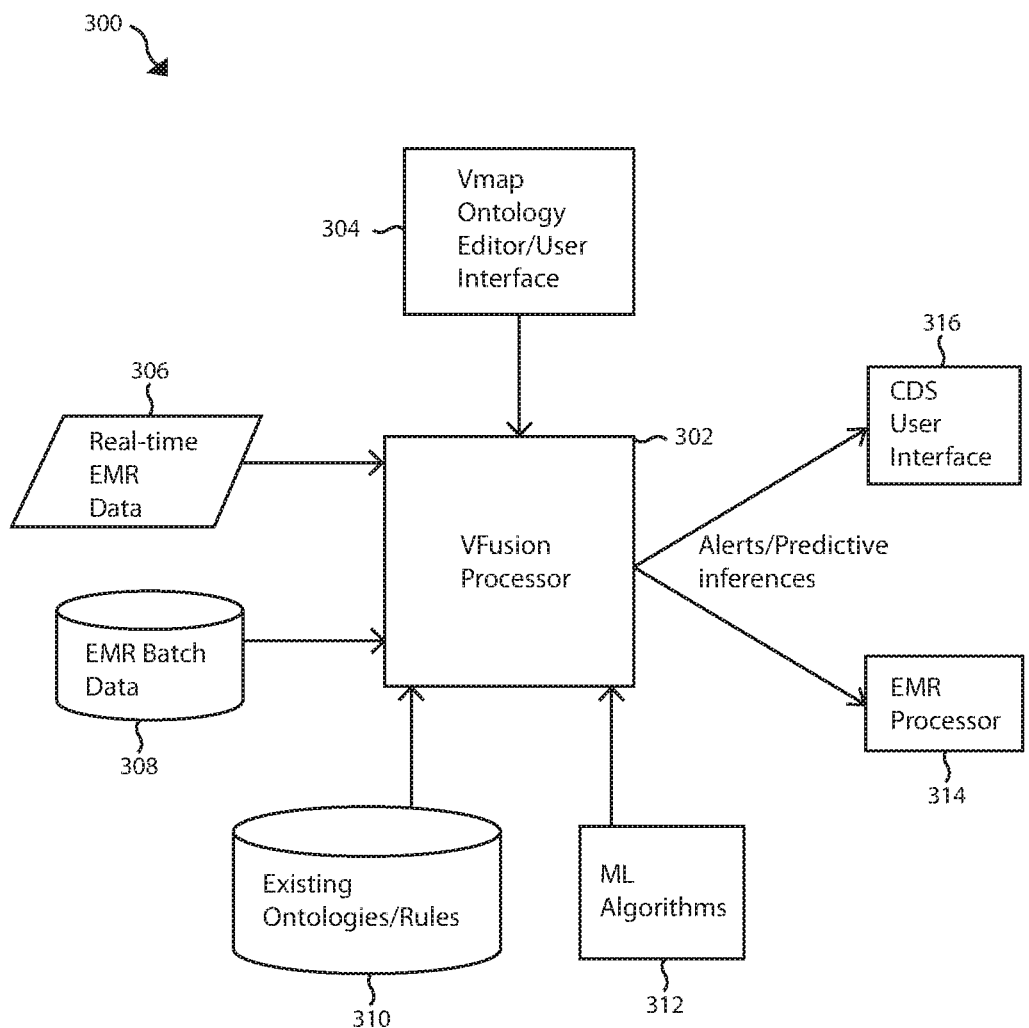
FIG. 3 is a system level overview of a processing platform according to an embodiment of the present disclosure.

FIG. 3 represent a "systems" view of the VFusion processing platform 302. From this perspective, a VFusion system inputs include: a) high level disease-specific ontology 304 expressed using concept maps called Vmaps (triples-based, directed hierarchical graph structures) representing reasoning used by expert clinicians in the management of a specific disease (e.g. sepsis); b) real-time EMR data streams 306 associated with patients under the care of the VFusion user to be monitored using VFusion; c) EMR batch data 308 used to train NLP and predictive algorithms associated with the disease; d) existing ontologies/rules 310 associated with disease-specific concepts; e) machine learning algorithms 312. VFusion outputs are actionable alerts/predictive inferences in support of patient management by users. Outputs can be either directed to specific user devices 316 (e.g. personal computers, tablets, phones, pagers, etc.) or interface directly to the EMR 314. This system includes a VFusion processor 302 and memory/storage devices, and external system and user interfaces. The central VFusion processor 302 can be a general processor, digital signal processor, application specific integrated circuit, field programmable gate array, analog circuit, digital circuit, combinations thereof, or other now known or later developed processor. The processor may be a single device or a combination of devices, such as associated with a network, distributed processing or cloud-based architectures. Any of various processing strategies may be used, such as multi-processing, multi-tasking, parallel processing, blockchain distributed knowledge management, or the like. The processor is responsive to instructions stored as part of software, hardware, integrated circuits, firmware, micro-code or the like.

Additional, different or fewer components may be provided, such as a mobile user device (e.g. tablets, smartphones). The system can be embodied in a powerful personal computer, institutional server and workstation environment, network to a cloud-based server, or other now known or later developed system elements for providing decision support in hospital settings. Interfaces to external EMR systems are supported using standards-based interfaces to hospital systems (e.g. HL7 messages). Automated assistance is provided to a bedside physician or nurse by monitoring real-time data associated with patients under the care of the user, invoking ontology-enhanced diagnostic rules and ML-based NLP and predictive models derived from historical data, and automatic generation of alerting messages that help clinicians identify at risk patients in critical care settings that may include emergency rooms, intensive care units (ICUs), telemetry units, post-surgical wards, etc. The automated assistance of VFusion is provided after subscription to a third-party service, purchase of the system, purchase of software, or payment of a usage fee.

The system could be used in one of more of the following manners: Mode 1) to create the disease-specific ontology guided expert system (rule engine) using graphical expressions developed by collaborating experts using the VFusion web-based Vmap ontology editor/user interface; Mode 2) used for training an ML algorithm using a disease specific ontology for enhanced retrospective training data semantic labeling and feature characterizations and providing a predictive algorithm as output; the disease specific ontology can also be used for training a ML-based NLP classifier to detect features/risk factors in free text notes; or Mode 3) applying the ontology-based rule engine as an expert system and pre-trained NLP and/or predictive algorithms in a CDS using prospective real-time data.

In Mode 1, the processor operates to provide ontology editor and user interface functionality to create/view/edit a disease-specific ontology and associated rules based on manually-derived high level conceptual graphs (Vmaps) and/or to augment/edit an existing upper level ontology with problem-specific data and rule logic. In this mode, the processor provides an intuitive graphical user interface and ontology editing functions needed for manually creating the clinical reasoning ontology (classes and rules) to be used in critical care settings. The Vmap editor is secure, auditable web-based tool enabling online crowdsourced disease specific ontology create/edit collaborations from one or more expert sources of information (e.g. a national clinical special interest workgroup). Decentralized peer-to-peer cryptographically enabled Vmap networks enable secure, auditable VFusion knowledge management. An expert's or experts' evidence-based knowledge, experience, heuristics and/or intuition may be used as an expert system to achieve an optimal balance of rule engine sensitivity/specificity and/or properly interpret EMR data through the "eyes" of expert teams of clinicians to achieve "clinically reasonable" diagnostic rule engine assessments and accurate ML-learnt probabilistic models/thresholds for alerting. To enable automated translation to formal computable ontological expressions, the graphical ontology editor employs templates based on the standards-based core ontology that guides the creation and editing of Vmaps. For example, these templates may predefine nodes and edges that allow clinicians to quickly add/modify class structures and/or add/modify rules based on user feedback. Through editor "ontology importation" services, the high level/core disease specific concepts can be automatically augmented with standardized granular level models based on existing medical ontologies for domains such as diseases, medications, labs, physiological findings, treatments, history, etc.

Modeled after human deductive reasoning, Vmaps capture concepts and rules at high levels of abstraction, characterizing patterns of activity, modeling expert knowledge, experience and intuitive-based anticipated outcomes, and new heuristic insights/lessons learned used to effectively deal with non-specific incomplete data, confounders, common causes of error, atypical patients, etc., in a user-friendly directed graph dialog, enabling VFusion to automatically combine these clinician expressed models with large, existing medical ontologies (e.g. SNOMED) to generate customized hierarchical computable ontologies that formalize "deep semantic" models. When combined with patient EMR data that instantiates the ontology forming a patient knowledgebase, these models serve as a highly competent expert system and can be used to parse/harmonize the contextual meaning of diverse raw clinical data, enabling inductive rule-based decision support and feature characterizations for machine learning closely reflecting complex human reasoning logic expressed in the Vmaps. The output of this process is OWL files with embedded rules.

Figure 4:
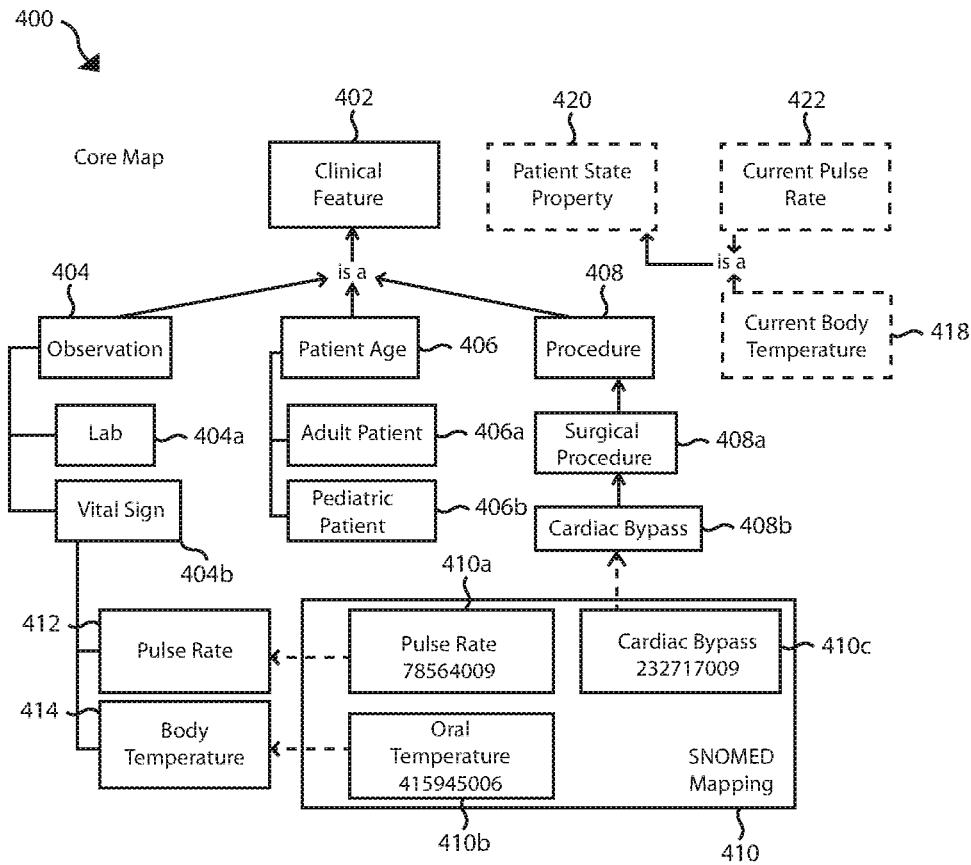
FIG. 4 is an example of a core clinical feature ontology in graphical form and the underlying OWL structures according to an embodiment of the present disclosure.

In FIG. 4 a small example of a core map 400 for selected concepts associated with sepsis management. A core clinical feature 402 ontology in graphical form and the underlying OWL structures showing the detailed association between core map concepts such as "Body Temperature 414" and SNOMED mapping 410 is shown.

In the traditional management of sepsis, the key clinical criteria for sepsis was defined in a 1992 guideline as a systemic inflammatory response syndrome (SIRS) "due to" infection. In this guideline SIRS is described as including "more than one" of the following clinical manifestations in adult patients:

Body temperature >38.0° C. or <36.0° C.
Heart rate >90 beats/min
Tachypnea >20 breaths/min or hyperventilation with PaCO2<32 mm Hg
White blood cell (WBC) count >12,000 cells/mm3; or <4,000 cells/mm3;

This guideline includes the statement: "These physiological changes should represent an acute alteration from baseline in the absence of other known causes for such abnormalities". This guideline is silent on the issue as to how to determine "more than one acute alteration from baseline" in the context of commonly asynchronous measurements of vitals, e.g. body temperature, pulse, respiratory rate and labs such as PaCO2, WBC that may be taken (or not) at differing times during a patient encounter in a typical hospital setting. The guideline is also not specific on the clinical determination of "due to" or the "absence of other known causes".

A typical rule-based hospital sepsis CDS system might be designed to continuously track EMR recordings of vital signs in a given ward of adult patients and, for example, trigger sepsis alerts whenever "acute alteration" elevated temperature and heart rate events occur, and evidence of an antibiotic or culture order is recorded. The details of how to calculate "acute alteration" when vitals and labs may be observed at differing times and intervals is frequently dependent on the clinical expertise and judgement of experts.

Figure 5:
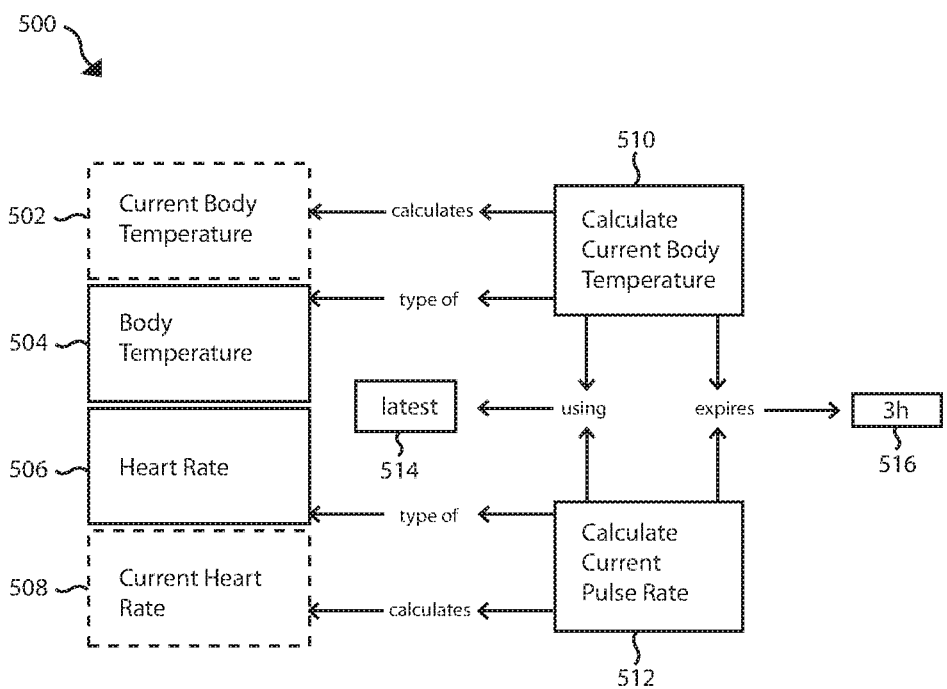
FIG. 5 is a small snippet of ontological logic that may be used to express clinical reasoning according to an embodiment of the present disclosure.
Figure 8A:
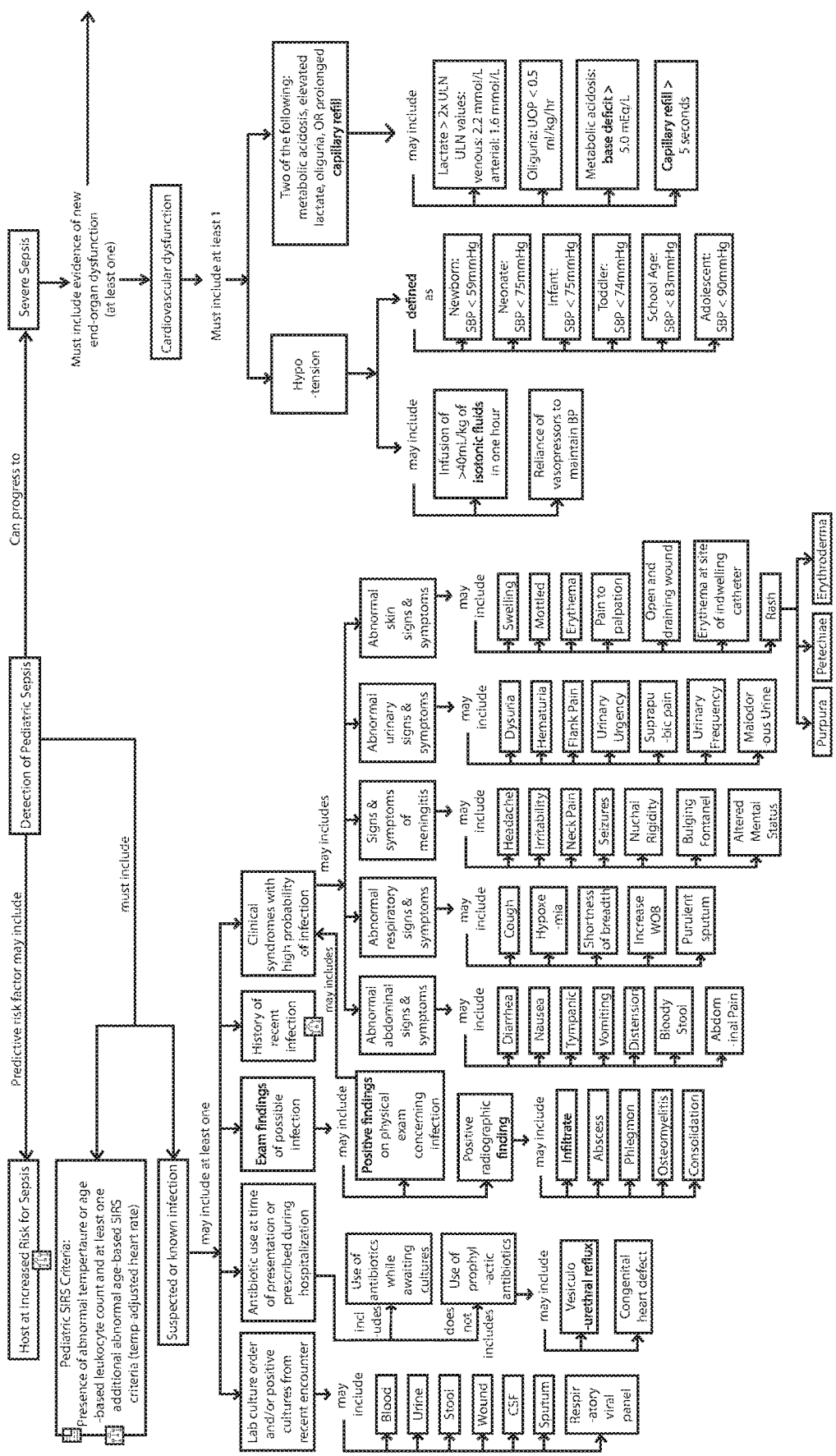
FIGS. 8a, b, c, d, e and f are sample Vmaps generated by the methods described in the present disclosure.
Figure 8B:
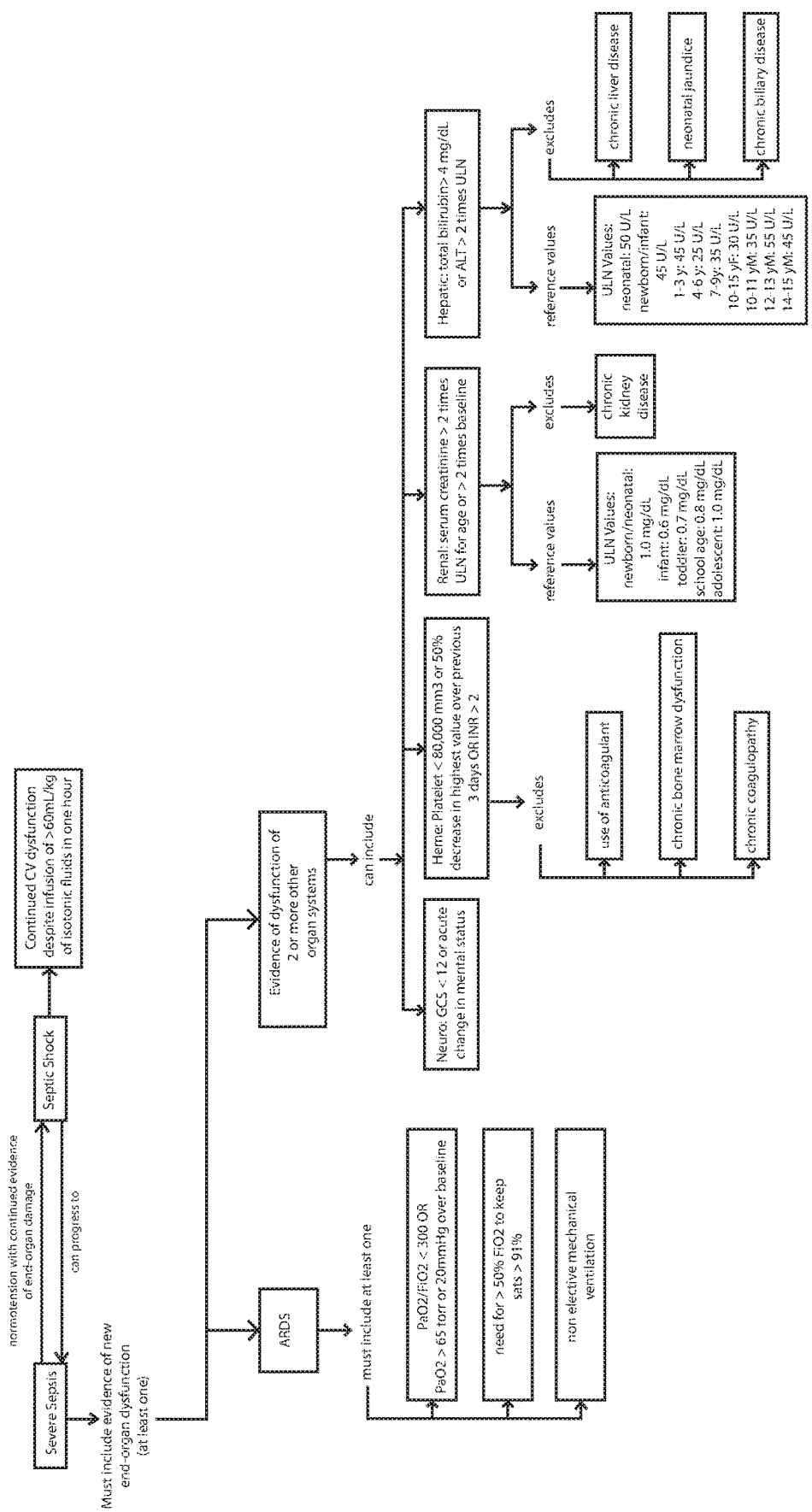
Figure 8C:
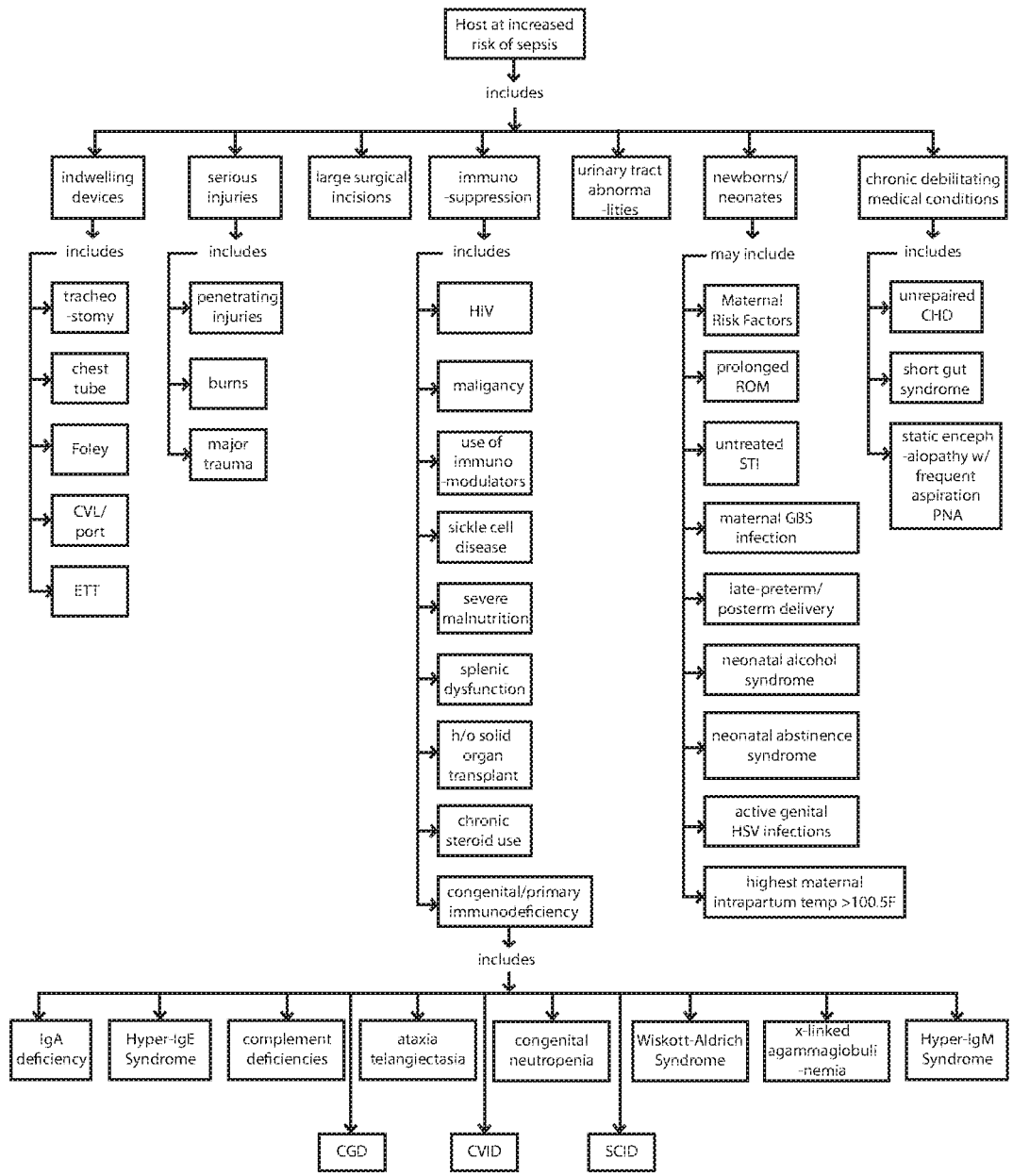
Figure 8D:
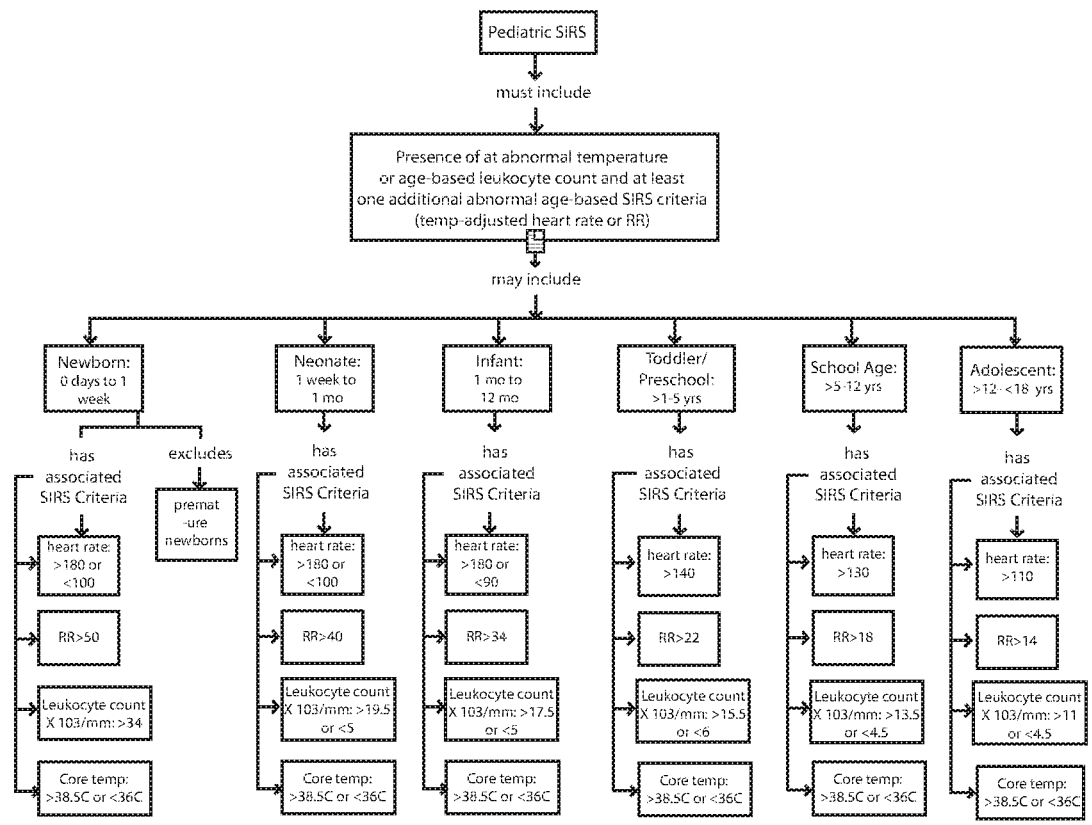
Figure 8E:
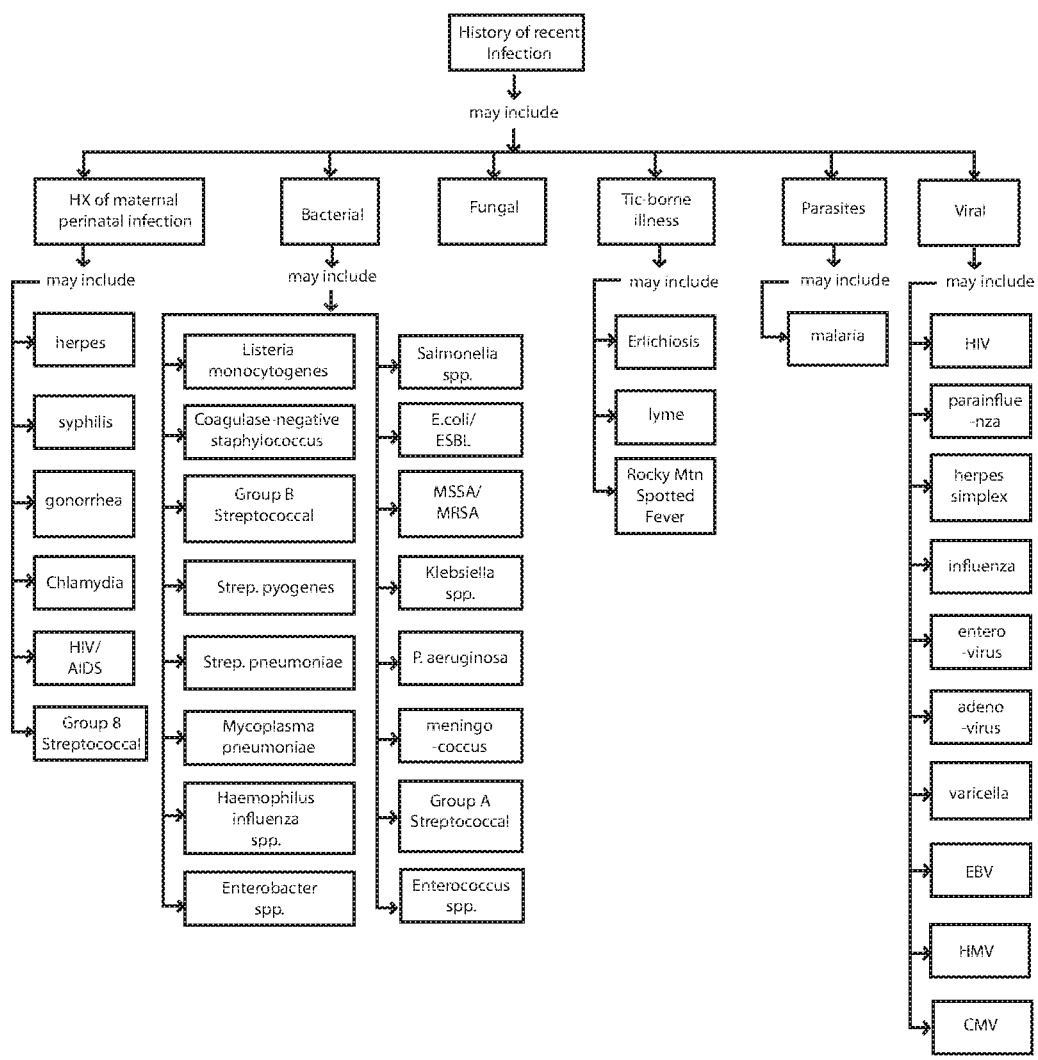
Figure 8F:
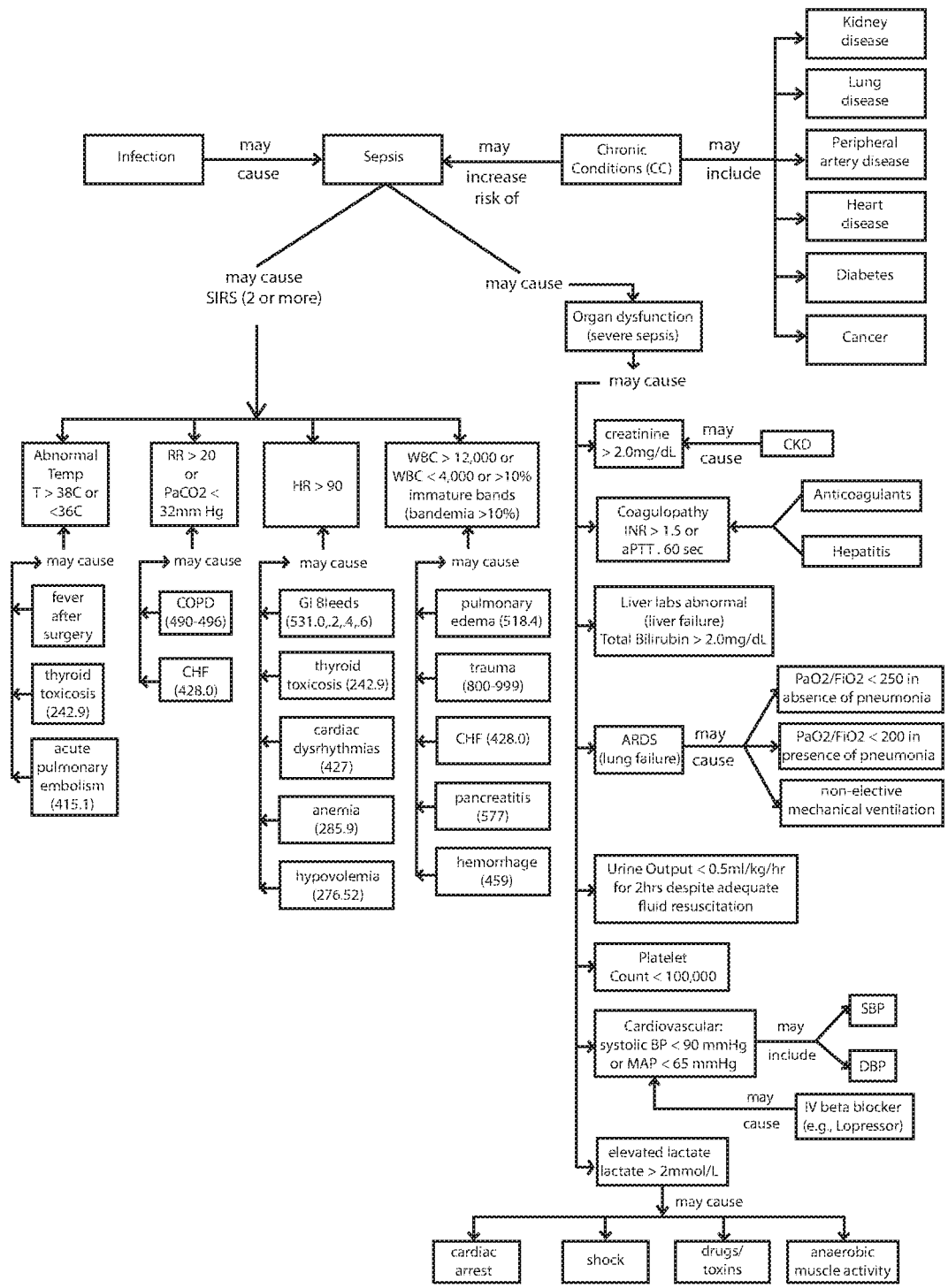

FIG. 5 illustrates a small snippet of ontological logic 500 that may be used to express clinical reasoning based on an expert's clinical interpretation of "acute alteration" in Body Temperature 504 and Heart Rate 506: e.g. "upon receipt of a new time-tagged temperature or pulse reading, calculate SIRS criteria using the latest available data within a 3-hour window". The illustrated ontological logic could be similarly extended to include respiratory rate (Tachypnea) in the reasoning as well as reasoning such as "use latest labs (PaCO2 or WBC) in this acute alteration logic if measured within last 24 hours". Upon experiencing either false positives or negatives, the logic could easily be modified to improve either sensitivity or specificity.

FIG. 6 illustrates ontological logic 600 that may be used to express clinical reasoning based on an expert's clinical interpretation of "in the absence of other known causes". For example, a typical rule-based hospital sepsis CDS system might be designed to continuously track EMR recordings of vital signs in a given ward of adult patients and, for example, trigger sepsis alerts whenever "concurrent" elevated temperature and heart rate events occur (observations taken within a short time window as described above). Given that it is known to experts that in post-surgical patients, temporary episodes of elevated body temperature and heart rate are common and "normal" responses to surgeries such as cardiac bypass surgeries, the ontology could be used to semantically characterize post-surgical elevated temperature and heart rate features as "non-infectious elevated temperature", "non-infectious elevated heart rate" and/or "non-infectious SIRS". In these cases, in the absence of other evidence of infection, which could be ascertained either by a query to clinician or textual analysis of progress notes, improved specificity of rule engine may be achieved by suppression of alerts for a specified post-surgical window of time (e.g. 72 hours). The illustrated ontological logic could be similarly extended to include expert clinical reasoning associated with other known non-infectious causes for SIRS (e.g. trauma, burns, pancreatitis, etc.).

FIG. 6 also illustrates the automatically generated First Order Logic rules equivalence to the graphically expressed reasoning that would be used in the CDS system to implement this logic in bedside alerting.

A memory is operable to store and reuse the resultant problem specific ontology which has a hierarchal node structure defining relative contribution of features at different levels of the clinical ontology. The processor employs the W3C Web Ontology Language (OWL) to represent problem-specific concepts and relationships and embedded rule engine constructs to support complex reasoning.

This combined representation of ontological classes and rules simplifies the merging of diverse ontologies into a single ontological resource to represent complex reasoning for use in ML and directly as a CDS expert system. A processor is operable to apply the disease-specific ontology consisting of OWL ontology classes and rules to monitor ongoing patient data streams and classify and reason over concepts documented in an electronic medical record of a patient to provide ongoing diagnostic assessments based on receipt of new patient data.

In Mode 2, the processor operates to create a predictive algorithm based on training data that has been semantically characterized by a disease-specific ontology. In this mode the processor provides an interface that can be used to import large samples of aggregated raw structured and unstructured EMR patient and employs a data processing "pipeline" to normalize/harmonize raw EMR data to a standard (e.g. map a medication name or number used in a proprietary EMR to a concept in the RXNORM medication ontology), semantically enrich diverse expression of concepts to the problem-specific ontology (e.g. recognize two drugs used to treat infections as members of the same class "antibiotics"), use NLP to identify signs/symptoms of infection expressed in free text notes, and use rules to contextually characterize enriched concepts (e.g. assert the antibiotic used was a "prophylactic antibiotic" or label outcomes (e.g. assert that a patient was is the class "severe sepsis" based on clinical criteria as opposed to reliance on administrative ICD codes that are frequently in error or missing).

FIG. 7 shows a small sample of tests used to measure the beneficial impact of combining disease specific Vmap-based ontologies and rules to pre-process/semantically characterize training data for machine learning. Sample predictive performance results 700 comparing the use of semantic characterizations against traditional EMR data features when used to train diverse, commonly used ML algorithms (e.g. logistic regression using regularization LASSO, Dynamic Bayesian Networks, and Cox regression using time dependent covariates). Our studies demonstrate consistent improvement in predictive performance (typically achieving AUCs greater than 0.95) when the sepsis ontology is used to condition the training data, reducing both outcomes "label noise" and predictor "feature noise" prior to machine learning, across diverse machine learning algorithms. Our predictive performance assessments are typically based on combinations of n-fold cross validation, independent test sets and comparisons against manually derived "gold standard" sets of cases.

FIGS. 8a, 8b, 8c, 8d, 8e and 8f are sample Vmaps (master map and sub maps) generated by the methods described in the present disclosure. This figure Vmaps were generated by using the methods described in paragraphs 0037-0040 above developed by expert clinicians in the disease specific field of pediatric sepsis. The Vmaps represent the complex highly specialized reasoning (rules, heuristics) used by these pediatricians in consideration of a constellation of time sensitive signs and symptoms indexed by patient age and maternal factors to diagnose and ultimately treat pediatric patients in critical care settings. The invention reduces these expressions to ontological classes and rules that can be automated to mimic the expressed expert reasoning in a bedside rule engine that is monitoring patient physiological data in real time CDS and generating alerts reflecting this expertise. The same expert disease specific ontology derived from the Vmaps may also be used to guide machine learning over large volumes of experiential data to recognize subtle patterns of physiological data associated with incipient sepsis hours before these signs manifest in measurements that are recognized by busy bedside clinicians. The derived learnt predictive model, if proven accurate and used in a bedside setting, would associate new data with these learnt patterns enabling clinicians to deliver disease preventive interventions.

Figure 9:
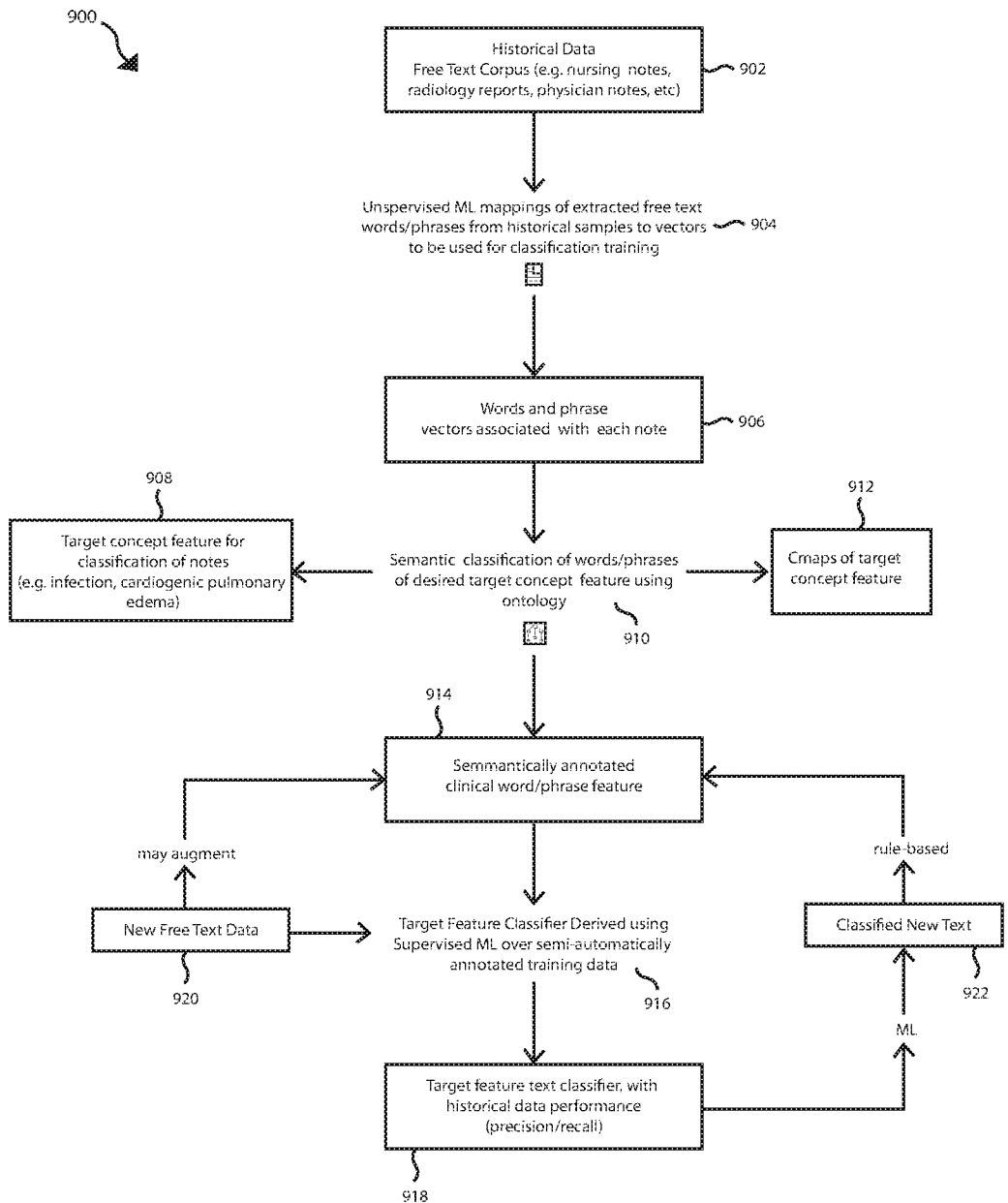
FIG. 9 shows an embodiment of the present disclosure of how ontology (e.g.

FIG. 9 shows an embodiment of the present disclosure of how ontologies (e.g. FIGS. 8a, 8c and 8e) is used to derive a machine learning based NLP algorithm to detect a target feature (e.g. infection) from free text notes. In Mode 2, the VFusion processor also includes a natural language processing (NLP) model derivation capability (FIG. 9) that uses the domain ontology to 1) create training data for machine learning consisting of raw unstructured EMR data mapped to vectors and 2) to encode the domain ontology as NLP rules that can be used for information extraction/document classification. In a manner like the overall CDS, the VFusion NLP sub-process also uses the combination of disease specific ontology/rules and machine learning to classify raw unstructured EMR data which is subsequently used as training data in combination with semantically characterized raw structured training data at the higher level CDS machine learning process. The unstructured EMR data includes free text from clinical reports, such as nursing notes, radiology reports, discharge summaries, etc. Word and phrases contained in specific text notes are mapped to vectors (embeddings) using well-established unsupervised neural networks technologies (word2vec/Glove). The vectorized training data combined with automatically generated ontologically-derived labels is further used in a supervised Machine Learning setting to generate a document classification predictive model using semantic characterizations of text features derived from the disease specific ontology. The predictive model can be further modified by enhancing the automatically created training data with data manually reviewed by human subject experts. The free-text training data can be used for the purposes of information extraction and/or document classification. A variety of Machine Learning and Natural Language Processing algorithms can be utilized, including neural networks and deep learning, support vector machines, logistic regression, conditional random fields, etc. to classify or extract information from free text notes. In the example of sepsis management, the challenge of recognizing infections (FIG. 8f) in early patient data is well recognized. An important data source for identification of infections may be radiology reports or nursing notes (FIG. 8a) that document the initial impressions (signs, symptoms, use of antibiotics, orders for cultures, patient history, etc.) of presenting patients. For example, a training dataset utilizing ontology classes and rules for identifying antibiotics extracted from nursing notes may be used to indicate the likely presence of an infection. Using the NLP processor, deep learning (neural networks) can be used to develop a comprehensive list of antibiotics, including abbreviations, misspellings, and brand names, together with their assertion status (administered, not administered, uncertain) and subsequently used with a ML classifier (e.g. SVM, Neural Networks, etc.) to semantically characterize free text notes (e.g. nursing notes, radiology reports, physician notes, procedure notes, etc.) as containing evidence of infection.

Figure 11:
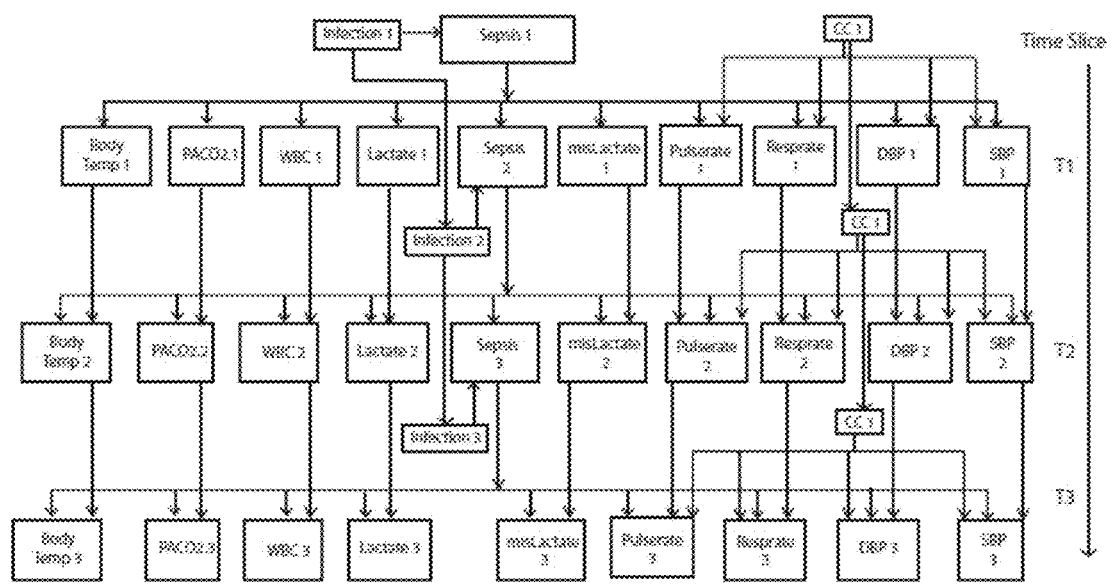
FIG. 11 shows an embodiment of the present disclosure of a specific Dynamic Bayesian Network to detect sepsis risk with topology (nodes and connections) guided by Vmap causal (FIG. 8f) ontology.

In Mode 2 the processor employs a large library of ML algorithms (e.g. regressions, classifiers, network-based algorithms, ensemble learning, and others) to derive and validate predictive models using the semantically characterized EMR data features. In machine learning, seeking to identify subtle physiological signatures associated with incipient disease such as sepsis in large volumes of data, reducing noise in critical features and labels by semantic characterizations guided by combined knowledge of collaborating multidisciplinary experts with years of disease-specific experience can only serve to improve the discriminating predictive ability of ML algorithms. Traditional machine learning algorithms are not able to incorporate background domain knowledge, but instead work with a sequence of instances, where each instance is represented by a single feature (attribute) vector describing the instance in the same manner irrespective of context. Disease specific ontologies allow the incorporation of expert domain knowledge in the machine learning process by contextually characterizing raw features, case labels and enable use of semantically characterized training data using this expert knowledge to train ML algorithms to identify/discriminate subclinical signatures of incipient life-threatening disease in the contextualized data. Moreover, causal network-based machine learning algorithms such as Dynamic Bayesian Networks (DBNs) provide a natural way to incorporate Vmap knowledge graphs into machine learning: they allow for a direct linkage between the node-link-node causal reasoning of Vmaps and the acyclic graph structure of a Bayesian network. Nodes in the DBN representing concepts in the Vmap (FIG. 8f) and "may cause" edges between Vmap nodes representing causal DBN links and dependencies (FIG. 11)

In Mode 3 (FIGS. 1b 1c) the processor applies the ontology-based rule engine and pre-trained ML NLP and predictive algorithms to assess real-time data for time-sensitive CDS in critical care environments. In this mode the processor storage media has stored therein data representing: 1) computer logic instructions executable by a programmed processor for rule-based computer assisted clinical decision support; and 2) computer logic instructions based on the machine learnt models influenced by the problem-specific ontology. As an example, the ML model may be a predictive logistic regression that is expressed as a set of model coefficients associated with predictive features for a probabilistic outcome that is calibrated to trigger alerts upon reaching a given threshold. Another ML example would be a time-series based DBN predictive model with trained conditional probabilities. Another ML example would be a NLP processor trained to detect infection risks from free text nursing and/or radiology reports. The processor also includes user specified logic such as filters, modes of communicating alerts, and feedback mechanisms that can be used to improve performance.

Although the present disclosure uses examples in the domain of sepsis, the system may be applied to any disease specific CDS useful in critical care punctuated by complex physiological changes that require immediate attention frequently driven by multiple simultaneous problems in critically ill patients. In busy care settings such as emergency departments and intensive care units, clinicians may be distracted from recognition of important changes essential for life-saving, frequently protocolized, interventions. CDS tools that reflect the expertise of practicing critical care clinicians and mimic the complex dual process reasoning over constellations of data elements commonly measured in critical care settings is envisioned. Examples of "difficult to manage" time sensitive diseases in critical care include sepsis, acute lung injury, hemorrhage, acute kidney disease, and acute brain injury among others.

It can be appreciated that the present disclosure introduces semantic technologies to significantly improve CDS performance: 1) for rule engines, "deep" semantic expressions of disease-focused expert reasoning can improve diagnostic performance of rule engines in management of complex critical conditions such as sepsis, ARDS, acute kidney disease, and by automation, simplify rule authoring of granular rules driven by existing ontologies and make possible production rule libraries consisting of hundreds/thousands/millions of rules; 2) for ML NLP and predictive modeling, semantically enhanced EMR training data that reduces label and feature noise can result in significantly improved predictive performance and generalizability of derived models.

Moreover, the processing "pipeline" described in the present disclosure simplifies recalibration of ML models with new patient data repositories and its semantic feature characterizations maintains the explanatory benefits of rule engine logic.

As rule engines and predictive analytics are used in clinical practice, observed deviations from actual experience (e.g. false positives or false negatives) can be used to continuously improve the rules and learnt algorithms. Machine learning can add predictive power by identifying subtle physiological signatures that may be present before clinical deterioration, when treatment might be more effective. Iterative enhancement of rules resulting from either poor rule engine performance or unexpected ML discovery of subtle atypical signatures in physiological data in new patients, may result in continuous improvement in both expert system rule engine and ML derived models that model the dual reasoning/learning processes of physicians . . . in effect physicians and machines "thinking and learning together"

In human decision making, the monitoring/self-checking capacity of a physician's System 2 type thinking (e.g. based on education/evidence base) may at times be triggered by a fast System 1 intuitive response to a new patient, that may result in a "rational override" of the initial fast response and in such cases, an improved diagnosis. However, physician inattentiveness, distraction, fatigue/tiredness, cognitive overload, and/or overconfidence may diminish System 2 surveillance.

Figure 10:
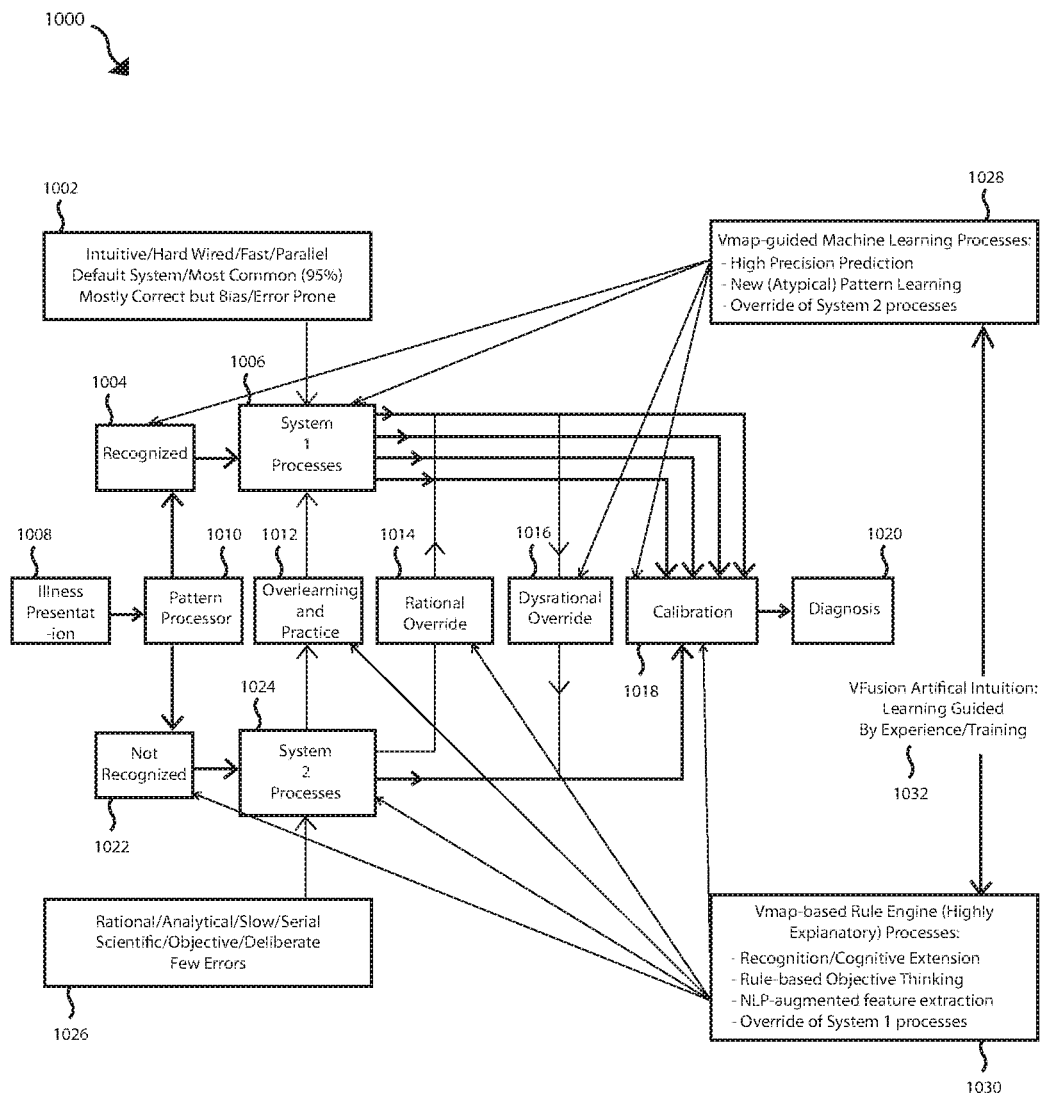
FIG. 10 shows an embodiment of the present disclosure of how the ontology guided rule engine and machine learning can be used to improve System 1 and System 2 decision making processes.

FIG. 10 illustrates a VFusion expert system/rule engine Mode 3 interventions containing 1) an expert system that may be useful in suggesting override of a potentially biased System 1 decision based on the collaborative expertise (simulating native System 2 monitoring by teams of experts), and similarly, 2) a ML-based predictive analytic that may represent a learned atypical pattern suggesting an override of a System 2 decision that may have failed to correctly recognize the pattern (simulating native System 1 experience-based intuition overriding guideline-based decisions). It can be appreciated that this hybrid ontology/ML approach can be used to directly address cognitive bias-induced errors (e.g. availability, anchoring, overconfidence)—the primary causes of such medical errors in urgent in-patient care settings. The present disclosure formalizes the interaction of System 2 rule-based thinking to train System 1 type thinking (pattern-matching NLP and predictive analytics) and is matched to the System 1/System 2 reasoning processes.

FIG. 11 shows an embodiment of the present disclosure of a specific Dynamic Bayesian Network to detect sepsis risk with topology (nodes and connections) guided by Vmap causal (FIG. 8f) ontology.

AI training based on interacting "deep" ontology-based expert systems and modern "deep learning algorithms focused in discovery of novel/useful patterns may be a model for all future AI initiatives in dealing with high risk real-world complexity in CC medicine.

VFusion Vmap editor gives physicians a comprehensive, immutable log and easy access to medical knowledge information across collaborators and institutions. Leveraging unique blockchain properties, VFusion manages authentication, confidentiality, change control, and data sharing-crucial considerations when handling potentially life-saving sensitive information. A modular design integrates with providers' existing EMR and local rule engine data storage solutions, facilitating interoperability across providers and making our system convenient and adaptable. Through a blockchain token offering, our system can incentivize medical stakeholders (critical care physicians, intensivists, hospitalists, researchers, etc.) to participate in the network as Vmap contributors and case reviewers. This provides them with access to aggregated knowledge data and provides token rewards for contributors to the knowledge base and those that participate in clinical case review. Tokens can be redeemed for VFusion licenses and services, and related items of value to clinical stakeholders.

The present invention has been described in particular detail with respect to the described possible embodiments. Those of skill in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead be performed by a single component.

The invention claimed is:

1. A method for creation, enhancement and use of a disease-specific ontology for computer assisted clinical decision support in critical care settings, the method comprising:
   capturing clinical knowledge of experts to create a core concept map using a graphical user interface and an ontology editor;
   creating a disease specific ontological model concept map comprising of complex expert rule-based reasoning;
   extending the core concept map with disease-specific reasoning concepts from the disease specific ontological model concept map to create a disease specific extended core map;
   extending the disease specific extended core map with existing medical ontologies and mappings that associate disease specific concepts with electronic medical record data;
   translating the disease specific extended core map and existing medical ontologies into web ontology language and rule artifacts to create disease-specific executable ontologies;
   ingesting raw electronic medical record data as historic population level batch files and patient-specific real-time data streams;
   normalizing and mapping the raw electronic medical record data to the disease-specific executable ontologies to create normalized data using semantic mapping and proprietary and disease-specific medical natural language processing engine;
   using the disease-specific executable ontologies to enrich the normalized coded and free-text data to create semantically enriched electronic medical record data;
   using the disease-specific ontology associated rules to semantically characterize the enriched data in the context of a specific disease;
   outputting disease-specific and semantically characterized clinical data and labels to be used in a semantically enhanced clinical decision support rule engine using real-time data in real-time mode to trigger alert;
   using semantically enhanced retrospective data as training data for a predictive machine learning process; and
   using both semantically enhanced rule-based and machine learning based models in a clinical decision support that support dual reasoning modes of clinicians.

2. The method of claim 1 further comprising using the user interface and ontology editor to express complex clinical reasoning and associated guidelines with sufficient structure for automated translation to computable logic without requiring any specialized training in tool usage.

3. The method of claim 2, further comprising extending the extended disease specific core map to include existing upper level core disease ontologies enabling interoperability with other related ontologies.

4. The method of claim 2, further comprising extending the extended disease specific core map to include comprehensive existing clinical Unified Medical Language System ontologies and electronic medical record-specific information models thus enabling disease-specific interpretation of data from any electronic medical record.

5. The method of claim 4, wherein using the disease-specific ontology associated rules further comprises utilizing a specific set of First Order Logic rules embedded in web ontology language to express executable complex reasoning logic that can mimic analytical clinician reasoning.

6. The method of claim 5, further comprising combining web ontology language rules/reasoner and rule engine constructs into a comprehensive disease specific ontology to support complex reasoning patterns and ontological structures including temporal event reasoning, truth maintenance, incremental reasoning and supporting assertion explanations.

7. The method of claim 1, further comprising using natural language processing that uses disease specific ontology, word embeddings, word frequencies, syntactic features, features derived from custom gazetteers or third-party tools, and machine learning over free text for the purposes of document classification and/or information extractions.

8. The method of claim 1, further comprising using the disease-specific ontology to semantically characterize training data to reduce outcomes "label noise" and be used with diverse supervised machine learning algorithms to derive enhanced predictive models.

9. The method of claim 1, further comprising using the disease-specific ontology to semantically characterize training data predictors to reduce "feature data noise" and be used with diverse machine learning algorithms to derive enhanced predictive models.

10. The method of claim 1, where the disease specific ontology is used to guide, constrain, supervise, and enhance rule engine alert sensitivity and specificity with associated high explanatory power, and experiential-based models derived by the semantically enhanced machine learning processes.

11. The method of claim 1, where the system uses recursive feedback from defined clinical subacute, acute, and administrative outcomes and patient visit history data for each processed patient record to improve the accuracy and predictive power of the machine and continually enhance both detection and prediction of the system as each new case is presented and processed.

12. The method in claim 1, where data from external sources including socioeconomic, familial, and environmental enhance the predictive power of the machine by developing the machine learning models.

13. The method of claim 12, wherein the machine learning based predictive models can detect subtle subacute signatures in characterized clinical data hours before clinical deterioration to support bedside clinical decision support.

14. The method of claim 1 wherein a blockchain token system is used to reward clinicians, patients, or administrative staff for reviewing cases and outcomes and for editing the concept map for disease specific ontologies, and wherein these healthcare stakeholders will earn tokens by reviewing cases and indicating whether they agree with or change a diagnosis and for editing a concept map to further enhance the clinical ontology and refine the diagnostic and predictive capabilities of the system, wherein a feedback loop is implemented to enhance learning by capturing human judgment through manual review, and wherein tokens are redeemable for services or licenses valued by the users of the system.

* * * * *